US011064978B2

(12) United States Patent
Kawashima et al.

(10) Patent No.: US 11,064,978 B2
(45) Date of Patent: Jul. 20, 2021

(54) ULTRASOUND DIAGNOSTIC APPARATUS AND OPERATION METHOD OF ULTRASOUND DIAGNOSTIC APPARATUS

(71) Applicant: OLYMPUS CORPORATION, Tokyo (JP)

(72) Inventors: Tomonao Kawashima, Hachioji (JP); Shoichi Matsui, Sagamihara (JP); Hiroshi Kodama, Hachioji (JP); Kenichi Nishina, Hachioji (JP); Hironaka Miyaki, Hino (JP); Hirotaka Eda, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 711 days.

(21) Appl. No.: 15/067,434

(22) Filed: Mar. 11, 2016

(65) Prior Publication Data
US 2016/0192909 A1    Jul. 7, 2016

Related U.S. Application Data

(63) Continuation of application No. PCT/JP2015/060458, filed on Apr. 2, 2015.

(30) Foreign Application Priority Data

Sep. 2, 2014   (JP) .............................. JP2014-178308

(51) Int. Cl.
| | | |
|---|---|---|
| *A61B 8/00* | (2006.01) | |
| *A61B 8/14* | (2006.01) | |
| *A61B 18/14* | (2006.01) | |
| *A61B 8/08* | (2006.01) | |

(Continued)

(52) U.S. Cl.
CPC .................. *A61B 8/54* (2013.01); *A61B 8/12* (2013.01); *A61B 8/14* (2013.01); *A61B 8/5207* (2013.01);

(Continued)

(58) Field of Classification Search
CPC .... A61B 8/54; A61B 8/12; A61B 8/14; A61B 8/5207; A61B 8/488; A61B 18/1477; A61B 2018/00333; A61B 2018/00595

(Continued)

(56) References Cited

U.S. PATENT DOCUMENTS

| | | | |
|---|---|---|---|
| 6,374,674 B1 * | 4/2002 | Mine .................... | A61B 8/14 |
| | | | 600/443 |
| 2001/0014771 A1 * | 8/2001 | Truwit ................ | A61B 90/11 |
| | | | 600/417 |

(Continued)

FOREIGN PATENT DOCUMENTS

| | | |
|---|---|---|
| CN | 101193594 A | 6/2008 |
| EP | 1804079 A2 | 7/2007 |

(Continued)

OTHER PUBLICATIONS

Japanese Office Action dated Sep. 29, 2015 issued in JP 2015-539985.

(Continued)

*Primary Examiner* — Christopher Koharski
*Assistant Examiner* — Katherine M McDonald
(74) *Attorney, Agent, or Firm* — Scully, Scott, Murphy & Presser, P.C.

(57) ABSTRACT

An ultrasound diagnostic apparatus includes: a beam former that drives an ultrasound transducer including two-dimensionally arranged vibration elements and that acquires ultrasound data of a three-dimensional space; a delay calculating circuit sets scan conditions including a drive delay amount of the beam former; a graphic circuit that generates an ultrasound slice image of a predetermined cut surface from the ultrasound data of the three-dimensional space; and a CPU that determines a focal length or a focal depth of the ultrasound according to a distance from the ultrasound transducer to the desirably set cut surface to set an amount (Continued)

of delay to cause the delay calculating circuit to change the scan conditions.

9 Claims, 12 Drawing Sheets

(51) Int. Cl.
*A61B 8/12* (2006.01)
*A61B 18/00* (2006.01)

(52) U.S. Cl.
CPC .......... *A61B 18/1477* (2013.01); *A61B 8/488* (2013.01); *A61B 2018/00333* (2013.01); *A61B 2018/00595* (2013.01)

(58) Field of Classification Search
USPC ........................................................ 600/439
See application file for complete search history.

(56) References Cited

U.S. PATENT DOCUMENTS

| | | | |
|---|---|---|---|
| 2007/0167769 A1 | 7/2007 | Ikuma et al. | |
| 2009/0018441 A1* | 1/2009 | Willsie | G01S 7/52034 600/437 |
| 2009/0275833 A1 | 11/2009 | Ikeda et al. | |
| 2010/0268067 A1* | 10/2010 | Razzaque | A61B 34/20 600/424 |
| 2015/0342561 A1* | 12/2015 | Takeda | A61B 17/3403 600/424 |
| 2015/0342572 A1* | 12/2015 | Tahmasebi Maraghoosh | A61B 8/54 600/424 |

FOREIGN PATENT DOCUMENTS

| | | |
|---|---|---|
| JP | 2000116651 A | 4/2000 |
| JP | 2006231035 A | 9/2006 |
| JP | 3847976 B2 | 11/2006 |
| JP | 2007175431 A | 7/2007 |
| JP | 2008289858 A | 12/2008 |
| JP | 2009233197 A | 10/2009 |
| JP | 4443672 B2 | 3/2010 |
| JP | 4488288 B2 | 6/2010 |
| JP | 2011024827 A | 2/2011 |

* cited by examiner

ULTRASOUND DIAGNOSTIC APPARATUS AND OPERATION METHOD OF ULTRASOUND DIAGNOSTIC APPARATUS

CROSS REFERENCE TO RELATED APPLICATION

This application is a continuation application of PCT/JP2015/060458 filed on Apr. 2, 2015 and claims benefit of Japanese Application No. 2014-178308 filed in Japan on Sep. 2, 2014, the entire contents of which are incorporated herein by this reference.

BACKGROUND OF THE INVENTION

1. Field of the Invention

The present invention relates to an ultrasound diagnostic apparatus that performs scanning with ultrasound and an operation method of the ultrasound diagnostic apparatus.

2. Description of the Related Art

An ultrasound diagnostic apparatus that transmits ultrasound into a living body and receives a reflected wave from living tissue to observe a state of the living body as an image while performing scanning (scan) by changing transmission and reception directions can observe conditions in the living body in real time. Therefore, various ultrasound diagnostic apparatuses have been proposed and widely used in recent years.

When the ultrasound diagnostic apparatus is used to observe, for example, a tumor, a treatment instrument, such as a puncture needle for obtaining cells or tissue and a cauterization needle for applying treatment, is used in some cases. In this case, for check a positional relationship between the tumor and the treatment instrument as well as the conditions of the living body around the treatment instrument, a technique of obtaining an image of a desired cut surface from volume data including a stereoscopically scanned ultrasound slice image is proposed.

For example, an ultrasound diagnostic apparatus and a control method of the ultrasound diagnostic apparatus is described in Japanese Patent Application Laid-Open Publication No. 2008-289858, wherein a model indicating various scan conditions in three-dimensional trigger scan, a position and an inclination of an arbitrary section, and a scan range as well as a screen for setting and changing these are displayed on a monitor, and these are set and changed by an input device.

A technique in an ultrasound diagnostic apparatus for observing an embryo is described in Japanese Patent Application Laid-Open Publication No. 2006-231035, wherein three-dimensional photographing conditions are automatically set based on information obtained from a two-dimensional image collected in advance.

A technique in a breast cancer screening apparatus is described in Japanese Patent Application Laid-Open Publication No. 2009-233197, wherein a deviation of a center position of breast is calculated from a two-dimensional image obtained by pre-scan, and a probe is moved and controlled based on a calculation result.

Furthermore, an ultrasound diagnostic apparatus is described for example in Japanese Patent Application Laid-Open Publication No. 2007-175431, wherein an ultrasound endoscope provided with a matrix array is inserted into a living body, volume data including a series of ultrasound slice images (hereinafter, original images) is acquired, and puncturing and biopsy of abnormal tissue are performed under an ultrasound slice image (hereinafter, reconstructed image) newly generated based on the acquired volume data. In the technique described in Japanese Patent Application Laid-Open Publication No. 2007-175431, when a surgeon designates a point on the original image, the apparatus sets a straight line as a puncture needle insertion axis based on the designated point, sets a surface for cutting the volume data so as to include the straight line, and generates the reconstructed image corresponding to the cut surface from the volume data. As a result, the entire puncture needle is rendered in the reconstructed image.

An ultrasound diagnostic apparatus in which an external ultrasound probe is connected is described in Japanese Patent No. 4443672, wherein a configuration is substantially same as in Japanese Patent Application Laid-Open Publication No. 2007-175431 described above. A technique is also described in Japanese Patent No. 4443672, wherein a cut surface perpendicular to the straight line (that is, perpendicular to the puncture needle) is set in addition to the cut surface including the straight line, and a reconstructed image of the cut surface is generated.

By the way, an example of a treatment method of living tissue includes energy treatment (RFA: radio frequency ablation), in which a therapeutic treatment instrument that outputs a high frequency electromagnetic wave is used to generate heat in an abnormal tissue to perform cauterization. There is also energy treatment (cryo) for freezing and coagulating abnormal tissue.

An ultrasound diagnostic apparatus is disclosed in Japanese Patent Application Laid-Open Publication No. 2011-024827, wherein an oscillating mechanical probe, a rotating mechanical probe, or a two-dimensional array probe is adopted, and when an arbitrary cut surface is designated on a three-dimensional image picked up in advance by one of the probes, ultrasound data of the cut surface is acquired again to generate a two-dimensional image of the cut surface (see, for example, paragraph [0016] of Japanese Patent Application Laid-Open Publication No. 2011-024827).

SUMMARY OF THE INVENTION

An aspect of the present invention provides an ultrasound diagnostic apparatus that performs scanning with ultrasound, the ultrasound diagnostic apparatus including: an ultrasound transducer including two-dimensionally arranged ultrasound vibration elements; a scanning section that drives the ultrasound transducer to generate the ultrasound and transmit the ultrasound for scanning in a three-dimensional space, and acquires ultrasound data of the three-dimensional space from the ultrasound received; a scan condition setting section that sets scan conditions of the scanning section including an amount of delay related to drive timing of the ultrasound vibration elements; a slice image generating section that generates an ultrasound slice image of a predetermined cut surface in the three-dimensional space from the ultrasound data of the three-dimensional space; a cut surface setting section that sets the cut surface at a desired position; and a control section that performs control of changing the scan conditions set by the scan condition setting section according to the cut surface set by the cut surface setting section, wherein the control section determines a focal length of the ultrasound or a focal depth of the ultrasound according to a distance from the ultrasound transducer to the cut surface and sets the amount of delay based on the determined focal length or focal depth.

An aspect of the present invention provides an operation method of an ultrasound diagnostic apparatus that performs scanning with ultrasound, the operation method including:

driving, by a scanning section, an ultrasound transducer including two-dimensionally arranged ultrasound vibration elements to generate the ultrasound and transmit the ultrasound for scanning in a three-dimensional space, and acquiring ultrasound data of the three-dimensional space from the ultrasound received; setting, by a scan condition setting section, scan conditions of the scanning section including an amount of delay related to drive timing of the ultrasound vibration elements; generating, by a slice image generating section, an ultrasound slice image of a predetermined cut surface in the three-dimensional space from the ultrasound data of the three-dimensional space; setting, by a cut surface setting section, the cut surface at a desired position; and performing, by a control section, control of changing the scan conditions set by the scan condition setting section according to the cut surface set by the cut surface setting section, wherein the control section determines a focal length of the ultrasound or a focal depth of the ultrasound according to a distance from the ultrasound transducer to the cut surface and sets the amount of delay based on the determined focal length or focal depth.

DETAILED DESCRIPTION OF THE PREFERRED EMBODIMENTS

Hereinafter, an embodiment of the present invention will be described with reference to the drawings.

First Embodiment

Figure 1:
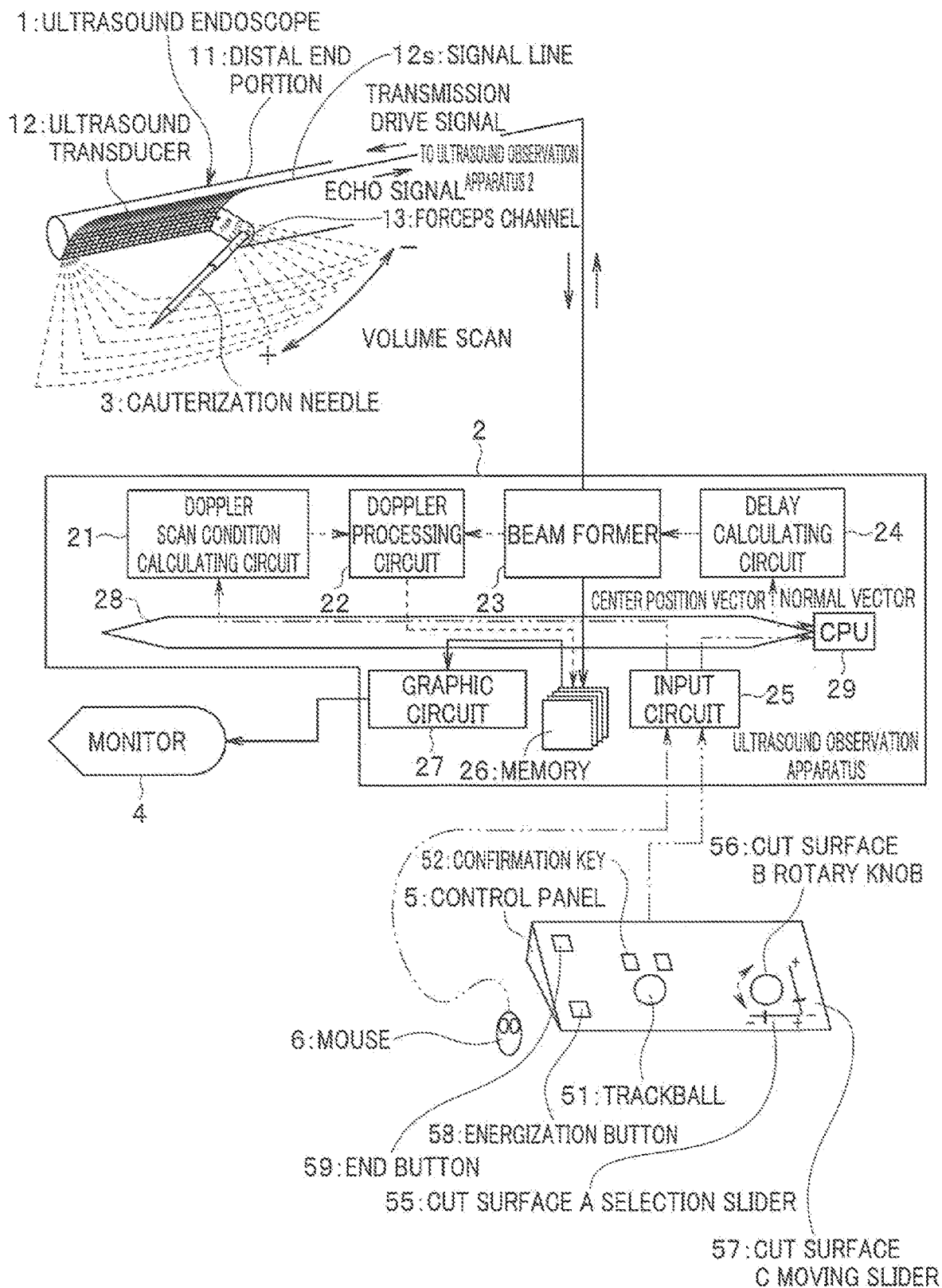
FIG. 1 is a diagram showing a configuration of an ultrasound diagnostic apparatus according to a first embodiment of the present invention.

FIGS. 1 to 14 illustrate a first embodiment of the present invention, and FIG. 1 is a diagram showing a configuration of an ultrasound diagnostic apparatus. Note that in FIG. 1, solid line arrows indicate flows of a transmission drive signal, an echo signal, echo data, and image data, dotted line arrows indicate flows of a color flow related signal and color flow related data, and alternate long and two short dashes line arrows indicate flows of cut surface setting, an ultrasound beam condition, a Doppler scan condition related signal, and Doppler scan condition related data, respectively.

The ultrasound diagnostic apparatus includes an ultrasound endoscope 1 that is an ultrasound probe, an ultrasound observation apparatus 2, a cauterization needle 3, a monitor 4, a control panel 5, and a mouse 6.

The ultrasound endoscope 1 includes an ultrasound transducer 12 on a distal end portion 11 of an elongated insertion portion inserted into a subject.

The ultrasound transducer 12 is formed by a two-dimensional ultrasound vibration element array in which a plurality of ultrasound vibration elements are two-dimensionally arranged. Here, an example of a specific arrangement of the ultrasound vibration elements in the two-dimensional ultrasound vibration element array includes a two-dimensional planar arrangement including a vibration element array parallel to an insertion direction and a vibration element array perpendicular to the insertion direction (however, the arrangement is not limited to this as described later).

Signal lines 12s are connected to respective ultrasound vibration elements of the ultrasound transducer 12, and each of the signal lines 12s is connected to the ultrasound observation apparatus 2. With this configuration, pulsed transmission drive signals for driving the ultrasound vibration elements and echo signals from the ultrasound vibration elements are transmitted and received between the ultrasound observation apparatus 2 and the ultrasound transducer 12 through the signal lines 12s. Therefore, each of the ultrasound vibration element included in the ultrasound transducer 12 can be driven at different timing and intensity, and the timing control and the intensity control can adjust a direction (direction of sound axis: here, the sound axis is a center axis of an ultrasound beam in scanning (scan) in one direction) of an ultrasound beam UB (see FIG. 2), a focal depth, and the like.

The insertion portion of the ultrasound endoscope 1 is further provided with a forceps channel 13 for inserting a treatment instrument, such as the cauterization needle 3 and a puncture needle (although an example of the cauterization needle 3 will be described below, the instrument is not limited to this). When the cauterization needle 3 is inserted to the forceps channel 13, the cauterization needle 3 extends into an ultrasound scan range of the ultrasound transducer 12 from a distal end side opening of the forceps channel 13 at the distal end portion 11. In this case, the forceps channel 13 is formed such that a center axis of the extending cauterization needle 3 is at a predetermined angle to an insertion axis of the insertion portion of the ultrasound endoscope 1. Furthermore, a positional relationship between the forceps channel 13 and an ultrasound vibration element array surface 12a (see FIG. 2) of the ultrasound transducer 12 is set such that a center axis direction of the cauterization needle 3 is rendered on one of cut surfaces A (see FIG. 3) when the cut surface A is rotated (see FIG. 10) around a y axis (the y axis is set to be parallel to an insertion axis direction of the insertion portion) as described later.

The ultrasound observation apparatus 2 includes a Doppler scan condition calculating circuit 21, a Doppler processing circuit 22, a beam former 23, a delay calculating circuit 24, an input circuit 25, a memory 26, a graphic circuit 27, a bus 28, and a CPU 29.

The CPU 29 is a control section that controls the entire ultrasound diagnostic apparatus including the ultrasound observation apparatus 2 and is also a computing section that performs necessary computation and the like. The CPU 29 transmits information related to a cut surface, such as a center position vector of the cut surface and a normal vector of the cut surface, that is set through the control panel 5 or the mouse 6, to the delay calculating circuit 24 through the bus 28.

Here, the bus 28 is a transmission path for transmitting a command, data, and the like from one location to another location in the ultrasound observation apparatus 2.

The delay calculating circuit 24 is a scan condition setting section that determines a transmission opening dimension of the ultrasound vibration element array surface 12a (arrangement range of the ultrasound vibration elements (the number of two-dimensionally arranged elements) used for the transmission of ultrasound), a reception opening dimension (arrangement range of the ultrasound vibration elements (the number of two-dimensionally arranged elements) used for the reception of ultrasound), a focal depth according to a distance from a transmission opening center of a cut surface (cut surface B, cut surface C, or the like described later), a focal length, a frequency filter, STC (sensitivity time control) that is a compensation of signal attenuation according to the depth, and the like. When rescan optimized for the cut surface is to be performed, the rescan may be performed by slice scan, or the rescan may be performed by volume scan. When the rescan is to be performed by the volume scan, the delay calculating circuit 24 further determines the number of focuses of multi-focus. The delay calculating circuit 24 then calculates an amount of delay related to drive timing of each ultrasound vibration element to obtain a highest spatial resolution on the cut surface instructed from the CPU 29 and transmits the amount of delay to the beam former 23.

The beam former 23 is a scanning section that generates a transmission drive signal to each of the ultrasound vibration elements arranged on the ultrasound vibration element array surface 12a based on the amount of delay received from the delay calculating circuit 24 and transmits the transmission drive signal to the ultrasound transducer 12.

The beam former 23 also receives echo signals from a plurality of ultrasound vibration elements of the ultrasound transducer 12 and applies signal processing to the echo signals based on the control by the CPU 29 and the delay calculating circuit 24. The beam former 23 transmits the processed signals to the memory 26 to be stored therein. In the present embodiment, the volume scan for acquiring a plurality of ultrasound slice images to acquire three-dimensional information of a subject is performed, and ultrasound volume data (hereinafter, simply called "volume data") is accumulated in the memory 26. Furthermore, rescan optimized for the cut surface is performed in the present embodiment as described later, and one of slice data of the cut surface obtained by the rescan or volume data including the cut surface is accumulated in the memory 26.

On the other hand, information of frequency change between the transmission drive signal from the beam former 23 and the echo signal is transmitted to the Doppler processing circuit 22 that is a Doppler processing section. The Doppler processing circuit 22 renders a blood stream based on Doppler effect.

The Doppler scan condition calculating circuit 21 is a Doppler scan condition setting section that sets Doppler scan conditions of the Doppler processing circuit 22. The Doppler scan condition calculating circuit 21 calculates scan conditions related to, for example, a color Doppler mode (however, not limited to the color Doppler mode) based on input setting of a user through the input circuit 25 and transmits the scan conditions to the Doppler processing circuit 22. Furthermore, the Doppler scan condition calculating circuit 21 changes conditions of the Doppler scan according to the cut surface set by the CPU 29 that is a cut surface setting section.

In this case, the conditions set by the Doppler scan condition calculating circuit 21 include a repetition frequency of the Doppler scan. A maximum value of the repetition frequency of the Doppler scan is determined according to the depth. Therefore, the maximum value of the repetition frequency can be obtained at each point in the cut surface B or the cut surface C described later to increase Doppler sensitivity to improve accuracy of color flow mapping.

Based on the conditions changed by the Doppler scan condition calculating circuit 21, the beam former 23 that is a scanning section uses an ultrasound beam to perform scanning in a three-dimensional space and/or in a cut surface to acquire new ultrasound Doppler data.

In this way, the Doppler processing circuit 22 that is a Doppler processing section allocates colors according to, for example, a flow rate of a blood stream to form a color image from the acquired ultrasound Doppler data (or acquired new ultrasound Doppler data) and transmits the color image to the memory 26. As a result, a color Doppler mode image is also accumulated in the memory 26.

The graphic circuit 27 is a slice image generating section that forms an ultrasound slice image from the volume data stored in the memory 26. The graphic circuit 27 further superimposes, for example, a color Doppler mode image on the formed ultrasound slice image and outputs the image to the monitor 4 that is a display section. As a result, the monitor 4 formed by, for example, a liquid crystal monitor displays an image of a color Doppler mode in which, for example, the blood stream with colors according to the flow rate is superimposed on a monochrome ultrasound slice image. In this case, when the ultrasound slice image is newly acquired according to the cut surface, the graphic circuit 27 superimposes the new ultrasound Doppler data on the new ultrasound slice image.

The input circuit 25 receives an inputted signal from the control panel 5 included in an operation portion and an inputted signal from the mouse 6 included in the operation portion.

The control panel 5 is a cut surface setting section (including a straight line setting section and a designation section) for setting a cut surface at a desired position. For example, the control panel 5 includes various operation members including a trackball 51, a confirmation key 52, a cut surface A selection slider 55, a cut surface B rotary knob 56, a cut surface C moving slider 57, an energization button 58, and an end button 59.

Figure 3:
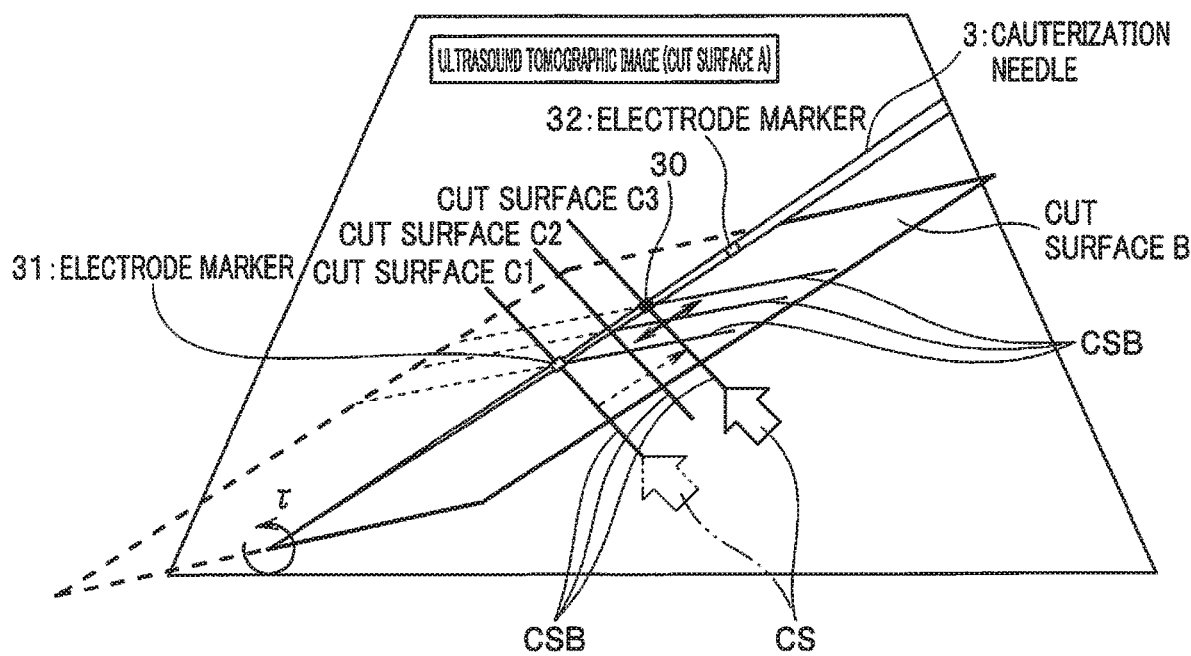
FIG. 3 is a diagram showing an example of an ultrasound slice image of a cut surface A displayed on a monitor in the first embodiment.

The trackball 51 and the confirmation key 52 are used for moving an arrow-shaped cursor (also called pointer) as shown in FIG. 3, designating an electrode position (position of dimple described later) using the cursor, and the like and also serve as a straight line setting section and a designation section. Note that the mouse 6 and an operation button provided on the mouse 6 may be used to perform various operations and settings performed by using the trackball 51 and the confirmation key 52. In this case, the mouse 6 also functions as the cut surface setting section (including the straight line setting section and the designation section) for setting a cut surface at a desired position.

Figure 10:
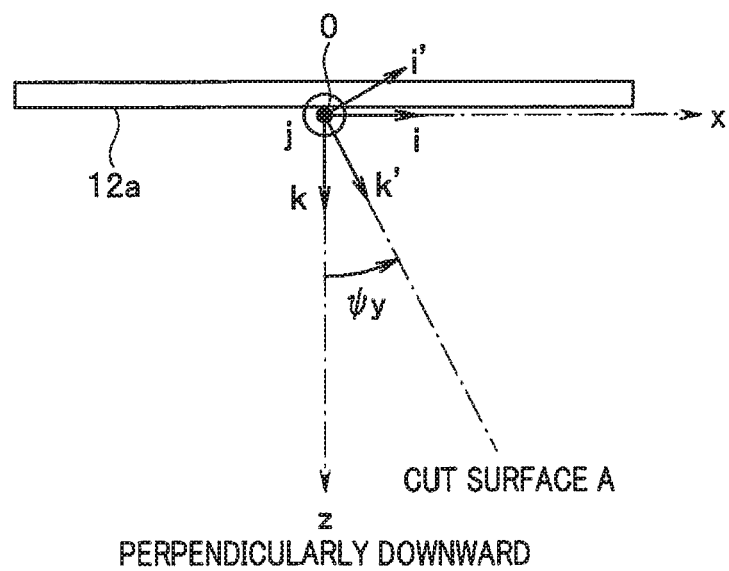
FIG. 10 is a diagram showing a positional relationship between the ultrasound vibration element array surface and the cut surface A according to the first embodiment.

The cut surface A selection slider 55 is an operation portion as a cut surface setting section that selects the cut surface A (see FIG. 3 and the like) described later. As a result of the operation of the cut surface A selection slider 55, an angle $\psi_y$ of the cut surface A relative to a zy plane shown in FIG. 10 (y axis in FIG. 10 is a front direction in the drawing) is set as an inputted value.

Figure 9:
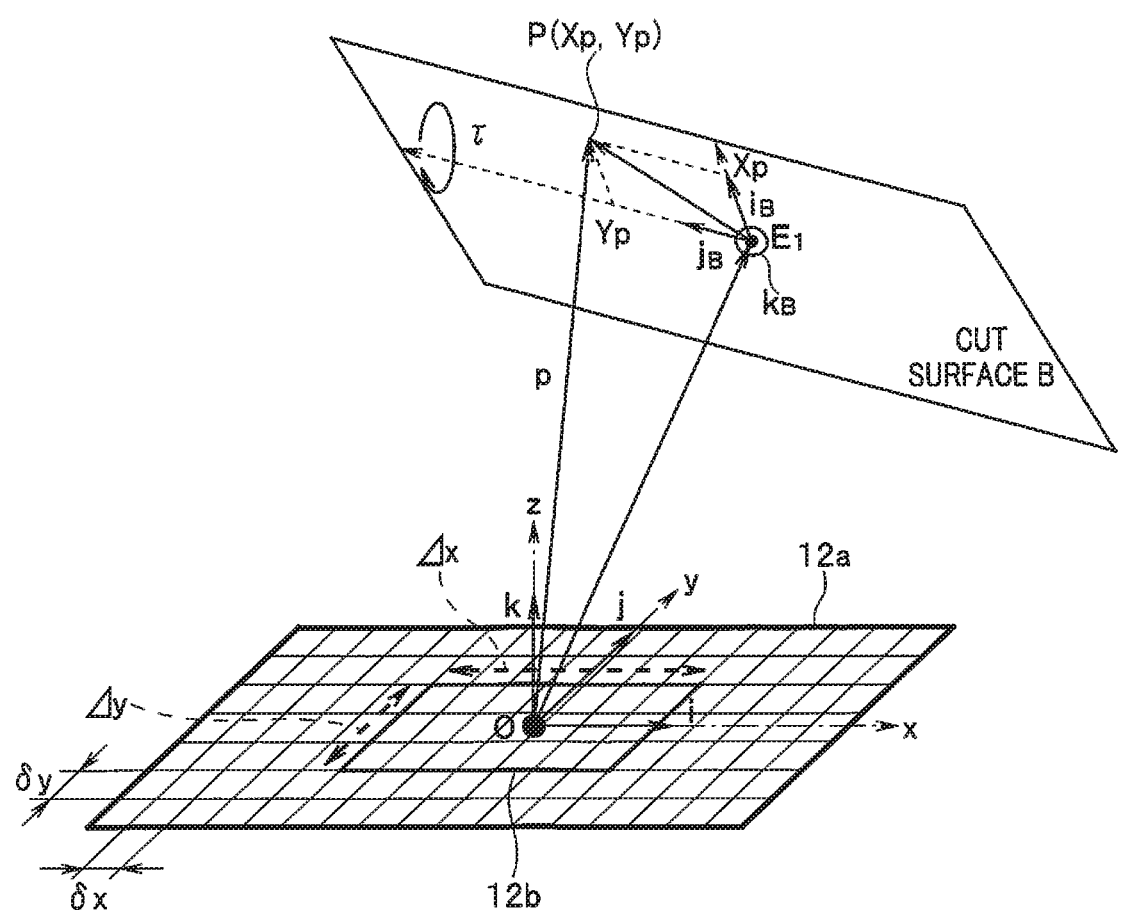
FIG. 9 is a diagram showing a positional relationship between the ultrasound vibration element array surface and the cut surface B according to the first embodiment.

The cut surface B rotary knob 56 is an operation portion as a cut surface setting section that rotates the cut surface B described later around the center axis of the cauterization needle 3. The cut surface B is selected so as to include the center axis of the cauterization needle 3, and as a result of the operation of the cut surface B rotary knob 56, a rotation angle τ around the center axis of the cauterization needle 3 of the cut surface B shown in FIGS. 3 and 9 is set.

The cut surface C moving slider 57 is an operation portion as a cut surface setting section that moves the cut surface C described later perpendicular to the center axis of the cauterization needle 3 (in addition, perpendicular to the cut surface A and the cut surface B), along the center axis of the cauterization needle 3. The cut surface C is selected such that a point that the center axis of the cauterization needle 3 passes through is set as a center of the surface, and as a result of the operation of the cut surface C moving slider 57, an amount of parallel movement L (see FIG. 4) of the cut surface C along the center axis of the cauterization needle 3 is set. The energization button 58 is an operation portion for energizing the cauterization needle 3, and the end button 59 is an operation portion for ending all processes at completion of treatment.

Figure 2:
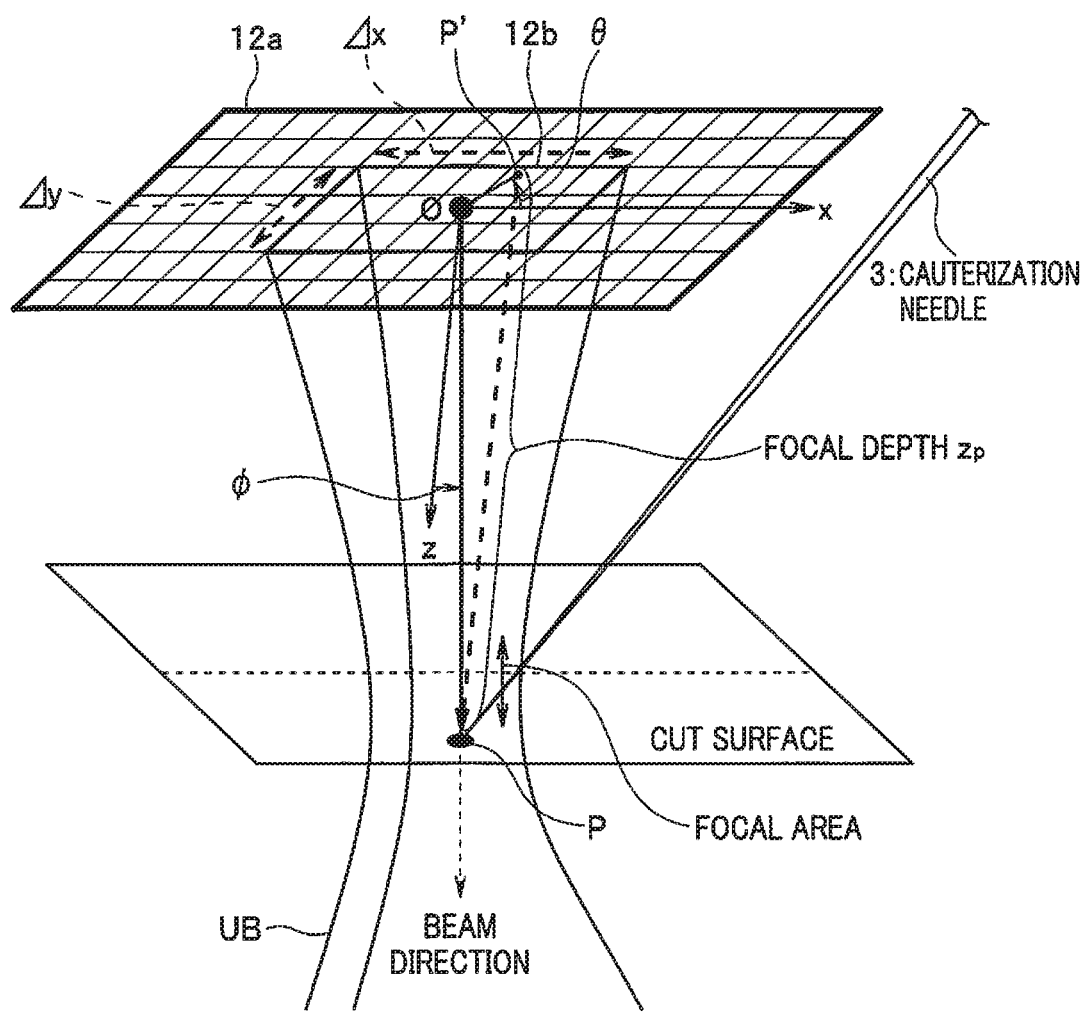
FIG. 2 is a diagram showing a positional relationship between an ultrasound vibration element array surface and a cut surface according to the first embodiment.

Next, FIG. 2 is a diagram showing a positional relationship between the ultrasound vibration element array surface 12a and the cut surface.

Although the ultrasound vibration element array surface 12a is a plane in the description here, the surface is not limited to the plane as described later.

A center of the ultrasound vibration element array surface 12a of the ultrasound transducer 12 is set as an origin O. An axis through the origin O and perpendicular to the ultrasound vibration element array surface 12a is set as a z axis. An axis through the origin O and parallel to the insertion axis direction of the insertion portion of the ultrasound endoscope 1 is set as a y axis (see FIG. 9). An axis through the origin O and perpendicular to the z axis and the y axis is set as an x axis. In this way, an orthonormal coordinate system O-xyz of a right-hand system is set.

A plurality of ultrasound vibration elements are two-dimensionally arranged on the ultrasound vibration element array surface 12a and are arranged in a matrix in an x axis direction and a y axis direction, for example.

In this case, not all of the ultrasound vibration elements arranged on the ultrasound vibration element array surface 12a are always used to generate the ultrasound beam UB. An ultrasound vibration element group arranged on a partial specific area (hereinafter, called an opening 12b) is used in some cases. For example, a rectangular opening with one pair of sides parallel to the x axis and the other pair of sides parallel to the y axis is used as the opening 12b. The number of ultrasound vibration elements of the opening 12b in the x axis direction will be expressed by Δx, and the number of ultrasound vibration elements in the y axis direction will be expressed by Δy. Although the numbers of opening elements Δx and Δy may be fixed values, the delay calculating circuit 24 may change the numbers according to the focal length or the like as described later. Note that although the same opening 12b may be used for transmission of ultrasound and for reception of ultrasound, openings with different sizes and shapes may be used.

Here, a cut surface in an arbitrary positional relationship with the ultrasound vibration element array surface 12a will be considered. The arbitrary cut surface is generally a cut surface intersecting with the sound axis. Therefore, even if the ultrasound slice image of the cut surface is created from the volume data accumulated in the memory 26, a high spatial resolution may not be always obtained. Therefore, the ultrasound beam UB optimized for the selected cut surface is used in the present embodiment to rescan the cut surface to acquire an ultrasound slice image with a higher spatial resolution.

As described, the cut surface is rescanned by transmitting and receiving the ultrasound beam UB such that a target point (arbitrary point P of FIG. 2) on the cut surface enters a focal area, and then a position of the arbitrary point P is moved by a predetermined amount on the cut surface to similarly scan the arbitrary point P after the movement. This is successively performed. In this way, an ultrasound slice image corresponding to the cut surface is acquired.

Therefore, the delay calculating circuit 24 determines a focal depth $Z_P$ for each direction I (θ, φ) of the ultrasound beam UB based on information stipulating the cut surface acquired from the CPU 29 (here, center position vector and normal vector of the cut surface) in order to optimize the ultrasound beam UB (more specifically, to put the arbitrary point P of the cut surface into the focal area of the ultrasound beam UB). Here, φ is an angle of OP relative to the z axis. Furthermore, θ is an angle of OP' relative to the x axis, wherein P' is a foot of a perpendicular line from the arbitrary point P to the ultrasound vibration element array surface 12a, that is, a projection point of the arbitrary point P on the ultrasound vibration element array surface 12a. Note that in FIG. 2, OP denotes the focal length, and P'P (parallel to the z axis) denotes the focal depth $Z_P$.

The ultrasound beam UB for the cut surface is basically optimized as follows. A formula of an arbitrary cut surface is described as in following equation 1 based on the information transmitted from the CPU 29 to the delay calculating circuit 24, wherein ($x_0$, $y_0$, $z_0$) is the center position vector of the cut surface in the O-xyz coordinate system, and (a, b, c) is the normal vector of the cut surface.

$$a(x-x_0)+b(y-y_0)+c(z-z_0)=0 \qquad \text{[Equation 1]}$$

Here, when $a \cdot x_0+b \cdot y_0+c \cdot z_0=-K$ is put, equation 1 is described as shown in following equation 2.

$$ax+by+cz+K=0 \qquad \text{[Equation 2]}$$

By the way, an amount of delay d of the ultrasound vibration elements arranged on the ultrasound vibration element array surface 12a can be described as shown in following equation 3 by using a multivariable function f with variables including a distance |p| (the distance |p|=OP is the focal length as described above) from the origin O that is the center of the ultrasound vibration element array surface 12a to the target point on the cut surface (arbitrary point P=(x, y, z) of FIG. 2) and a direction (θ, φ) from the origin O to the arbitrary point P. Note that the amount of delay d further depends on the position of the ultrasound vibration elements in the ultrasound vibration element array surface 12a. However, a formula of the dependency will be described later, and the dependency is not described in equation 3.

$$d=f(|p|,\theta,\phi)$$ [Equation 3]

In this way, the condition (here, amount of delay d) related to the scanning with the ultrasound beam UB varies with the direction (direction of OP) of the sound axis of the ultrasound beam UB.

First, the distance |p| is described as shown in following equation 4 based on the coordinates (x, y, z) of the arbitrary point P constrained by equation 2.

$$|p|=\sqrt{x^2+y^2+z^2}$$ [Equation 4]

Furthermore, θ is uniquely determined in a range of 0≤θ≤2π based on following equation 5.

$$\cos\theta = \frac{x}{\sqrt{x^2+y^2}}$$ [Equation 5]

$$\sin\theta = \frac{y}{\sqrt{x^2+y^2}}$$

In addition φ is determined based on following equation 6.

$$\cos\phi = \frac{z}{|p|} = \frac{z}{\sqrt{x^2+y^2+z^2}}$$ [Equation 6]

In this way, the delay conditions for optimizing the ultrasound beam UB for the arbitrary point P on the cut surface are obtained by equation 3 (variable values to be assigned to equation 3 are obtained by equations 4 to 6). Therefore, equation 3 can be used for each arbitrary point P on the cut surface under the constraint condition of equation 2 to optimize and transmit the ultrasound beam UB. An ultrasound slice image with a high spatial resolution can be acquired, in which the entire cut surface is optimized.

Note that the optimization of the ultrasound beam UB for the cut surfaces B and C selected by the operation system of the present embodiment will be more specifically described later.

Figure 8A:
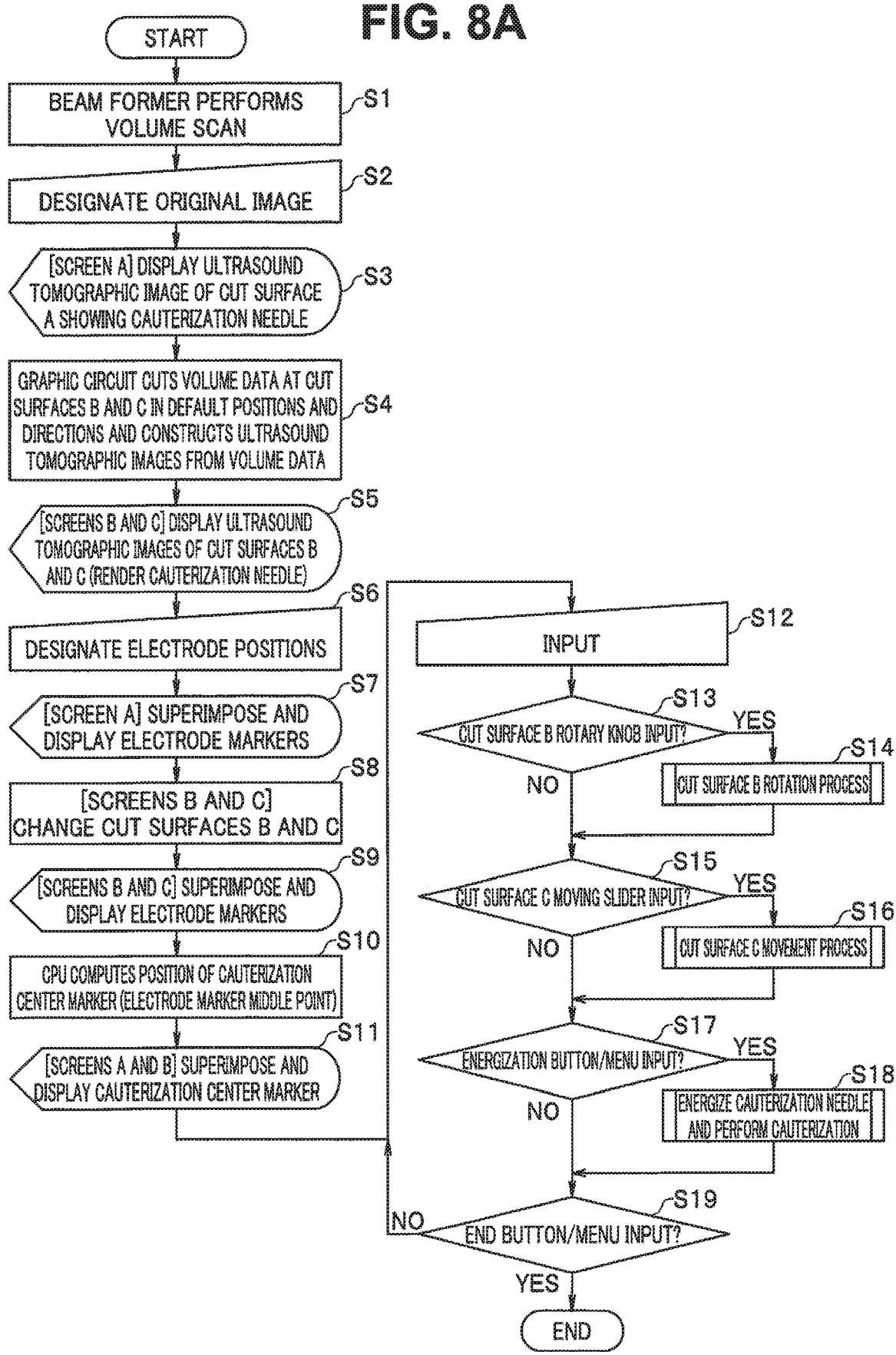
FIG. 8A is a flowchart showing operation of the ultrasound diagnostic apparatus according to the first embodiment.

FIG. 8A is a flowchart showing operation of the ultrasound diagnostic apparatus. FIG. 8A shows a flow of the entire operation of the ultrasound diagnostic apparatus, and details of a "cut surface B rotation process" and a "cut surface C movement process" that are part of the operation will be described later with reference to FIGS. 8B and 8C.

When the process is started, the beam former 23 performs volume scan based on control by the CPU 29 (step S1).

Specifically, when the scan is started, the beam former 23 transmits a transmission drive signal with a pulsed voltage provided with a delay of each ultrasound vibration element to the ultrasound transducer 12 based on control by the CPU 29 and the delay calculating circuit 24.

The ultrasound vibration elements arranged in the opening 12b (see FIG. 2) receive the transmission drive signal that is an excitation signal with a pulsed voltage from the beam former 23 and convert the transmission drive signal into ultrasound that is a compressional wave of a medium. The ultrasound excited by each ultrasound vibration element in this case forms one ultrasound beam UB (see FIG. 2) when the ultrasounds are superimposed in the subject (the delay calculating circuit 24 provides the delay to each transmission drive signal to form this ultrasound beam UB). In this way, the ultrasound beam UB generated from the ultrasound transducer 12 is transmitted to an area of interest of the subject. A reflected wave from the area of interest of the subject passes through a route opposite the ultrasound beam UB and reaches each ultrasound vibration element of the ultrasound transducer 12. Each ultrasound vibration element converts the reflected wave into an electrical echo signal and transmits the echo signal to the beam former 23. The beam former 23 amplifies the received echo signal and performs phasing addition.

The one-point (one-direction) scan based on the ultrasound beam UB is performed for a plurality of times by changing the direction to perform surface scan of obtaining one ultrasound slice image, and the surface scan is further performed for a plurality of times by changing the direction to perform volume scan. A plurality of ultrasound slice images acquired by the volume scan are stored in the memory 26, and three-dimensional volume data of the area of interest in the subject is formed.

Next, the user operates the cut surface A selection slider 55 to select the cut surface A (step S2). Here, the cut surface A is one of the ultrasound slice images obtained by the volume scan of step S1, that is, an ultrasound slice image after scanning along the sound axis, which is an image with a high spatial resolution. The user selects the cut surface A by finding and selecting a surface rendering the cauterization needle 3 while observing the ultrasound slice image of the cut surface A displayed on the monitor 4. The angle ψ$_y$ (see FIG. 10) of the cut surface A is set by the selection operation of step S2.

When the selection is made, the ultrasound slice image (see FIG. 3) of the cut surface A rendering the cauterization needle 3 is displayed on the monitor 4 (step S3). Here, FIG. 3 is a diagram showing an example of the ultrasound slice image of the cut surface A displayed on the monitor 4.

The graphic circuit 27 constructs ultrasound slice images by cutting the volume data at the cut surfaces B and C with default positions and directions (step S4).

Here, the default position of the cut surface B is set such that the center of the cut surface B coincides with the center of the cut surface A (coincides with a point at the center of the height in the vertical direction and the center of the width in the horizontal direction). The default direction of the cut surface B is set such that the cut surface B includes a direction determined in advance from a design value expected when the cauterization needle 3 projects to the cut surface A (for example, direction indicated by "cauterization needle 3" in FIG. 3) and such that a normal line of the cut surface B is parallel to the cut surface A.

The default position of the cut surface C is set such that the center of the cut surface C coincides with a middle point of the cut surface B in the "direction determined in advance". The default direction of the cut surface C is set such that the cut surface C is perpendicular to the "direction determined in advance" and that an upper direction of the cut surface C is parallel to the cut surface A.

When the cauterization needle 3 is to be automatically detected from the ultrasound slice image of the cut surface A by performing image processing or the like, the cut surface B at the default position including the cauterization needle 3 and the cut surface C at the default position perpendicular to the cauterization needle 3 may be selected at this point. When the automatic detection is not to be performed (or cannot be performed), the process may wait for selection of an appropriate default position until the user designates an electrode position in step S6 described later.

Figure 4:
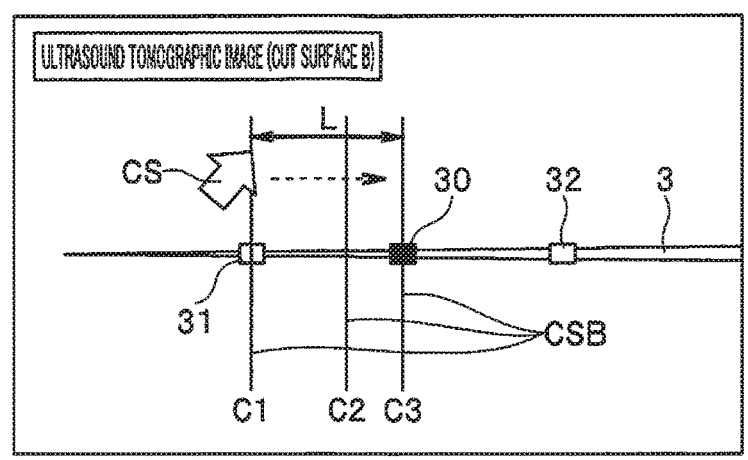
FIG. 4 is a diagram showing an example of an ultrasound slice image of a cut surface B displayed on the monitor in the first embodiment.
Figure 5:
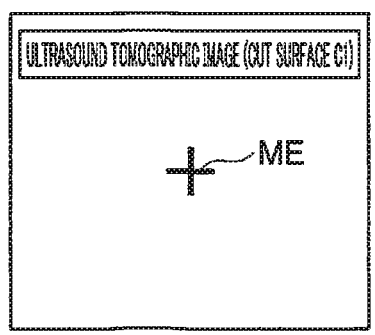
FIG. 5 is a diagram showing an example of an ultrasound slice image of a cut surface C1 displayed on the monitor in the first embodiment.
Figure 6:
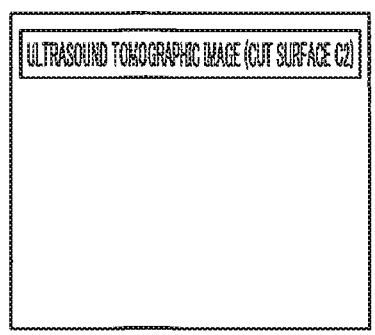
FIG. 6 is a diagram showing an example of an ultrasound slice image of a cut surface C2 displayed on the monitor in the first embodiment.
Figure 7:
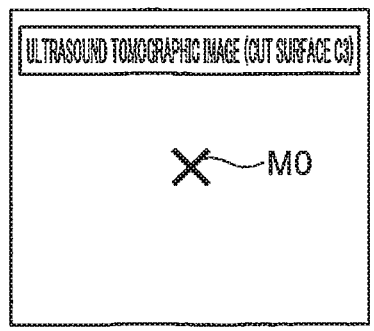
FIG. 7 is a diagram showing an example of an ultrasound slice image of a cut surface C3 displayed on the monitor in the first embodiment.

Then, the ultrasound slice image of the cut surface B (see FIG. 4) and the ultrasound slice image of the cut surface C (see FIGS. 5 to 7) are displayed on the monitor 4 (step S5). In this way, the ultrasound slice image of the cut surface A as shown in FIG. 3 (displayed part will be appropriately called a screen A), the ultrasound slice image of the cut surface B as shown in FIG. 4 (displayed part will be appropriately called a screen B), and an ultrasound slice image of the cut surface C as shown in FIGS. 5 to 7 (displayed part will be appropriately called a screen C) are aligned and simultaneously displayed on the monitor 4, for example. Here, FIG. 4 is a diagram showing an example of the ultrasound slice image of the cut surface B displayed on the monitor 4, FIG. 5 is a diagram showing an example of the ultrasound slice image of a cut surface C1 displayed on the monitor 4, FIG. 6 is a diagram showing an example of the ultrasound slice image of a cut surface C2 displayed on the monitor 4, and FIG. 7 is a diagram showing an example of the ultrasound slice image of a cut surface C3 displayed on the monitor 4. Here, cut surfaces C1 to C3 are three examples of the cut surface C. However, instead of aligning and displaying the images, the user may be able to switch which one of the ultrasound slice images of the cut surfaces is to be displayed on the monitor 4.

As a result of the process described above, the cauterization needle 3 is rendered in at least the ultrasound slice image of the cut surface A shown in FIG. 3 along the center axis of the cauterization needle 3. In this state, the user designates the electrode position of the cauterization needle 3 (step S6).

A bipolar cauterization needle 3 is illustrated in the examples shown in FIGS. 3 and 4, and two electrodes with different polarities are provided on the cauterization needle 3 along the center axis. A dimple is formed on each of the electrodes, and the electrodes can be easily viewed as bright points on the ultrasound slice image. Therefore, the user performs operation of using the trackball 51 and the confirmation key 52 that function as a straight line setting section and a designation section or operation of using the mouse 6 that functions as a straight line setting section and a designation section to designate the bright points corresponding to two electrodes. The graphic circuit 27 sets a straight line passing through the designated two bright points on the cut surface A.

Note that although the straight line setting section designates a plurality of points to set the straight line on the ultrasound slice image of the cut surface generated by the graphic circuit 27 that is a slice image generating section here, the arrangement is not limited to this, and points and directions may be designated to set the straight line.

Furthermore, if the dimples are provided on other positions instead of the positions of the electrodes, a positional relationship between the electrodes and the dimples may be stored in the ultrasound observation apparatus 2. When the user designates the positions of the dimples, the CPU 29 that functions as a calculating unit may automatically compute the electrode positions and the position of the cauterization center described later from the positions of the dimples and may superimpose electrode markers and a cauterization center marker described later based on a computation result.

In response to the designation operation, the graphic circuit 27 that functions as a marker superimposing section superimposes and displays an electrode marker 31 on a distal end side and an electrode marker 32 on a proximal end side on the ultrasound slice image of the screen A as shown in FIG. 3 based on the control by the CPU 29 (step S7).

Furthermore, the graphic circuit 27 changes the direction of the cut surface B such that the cut surface B includes the straight line set by the straight line setting section and that the normal line of the cut surface B is parallel to the cut surface A. Then, the graphic circuit 27 changes the position and the direction of the cut surface C such that the cut surface C is perpendicular to the straight line set by the straight line setting section and that the upper direction of the cut surface C is parallel to the cut surface A. Furthermore, the graphic circuit 27 makes a change such that the center of the cut surface C coincides with the electrode position on the distal end side if the cauterization needle 3 is bipolar and changes and moves parallel the position of the cut surface C such that the center of the cut surface C coincides with one electrode position if the cauterization needle 3 is monopolar (step S8). Note that these are not changed if the default positions and directions are like this.

In this way, regardless of whether there is automatic detection of the cauterization needle 3, the cut surface B of the ultrasound slice image displayed on the screen B is set on a surface including the center axis of the cauterization needle 3, and the cut surface C of the ultrasound slice image displayed on the screen C is set on a surface perpendicular to the center axis of the cauterization needle 3.

Then, the electrode marker 31 and the electrode marker 32 on the proximal end side are also superimposed and displayed on the ultrasound slice image of the screen B as shown in FIG. 4 (step S9).

Note that a cursor bar CSB indicating a line of intersection of the cut surface C and the cut surface A and a cursor CS that is a pointer moved by the trackball 51 or the mouse 6 are displayed on the screen A. Here, although FIG. 3 illustrates the cut surface A, the cursor bar CSB indicating the line of intersection of the cut surface C and the cut surface A, and the cursor CS, as well as the rectangle indicating the cut surface B and the cursor bar CSB indicating the line of intersection of the cut surface C and the cut surface B for the convenience of the description, the rectangle and the latter cursor bar CSB are not displayed on the screen A.

The screen B also displays the cursor bar CSB indicating the line of intersection of the cut surface C and the cut surface B and the cursor CS that is a pointer moved by the trackball 51 or the mouse 6.

The cauterization range with the bipolar electrodes in general is like a spheroid with a center at a middle point of the two electrodes. Therefore, the CPU 29 computes a position of the middle point of the two electrodes as a cauterization center position (step S10).

Based on the control by the CPU 29, the graphic circuit 27 superimposes and displays the cauterization center marker 30 at the computed cauterization center position on the screen A and the screen B as shown in FIGS. 3 and 4 (step S11).

Note that the cauterization needle 3 is bipolar in the example described here, and the cauterization center position is computed from the position of the two electrodes and displayed. However, the cauterization needle 3 may be monopolar, and in this case, a position of a monopolar electrode is set at the cauterization center position, and the electrode marker or the cauterization center marker 30 is superimposed and displayed.

Subsequently, the user carries out one of following operations of I to IV to perform input to the ultrasound diagnostic apparatus (step S12).

I. For example, the user operates the cut surface B rotary knob 56 to check circumstances around the cauterization needle 3, more specifically, whether a blood vessel, an organ, or the like that should not be damaged exists around the cauterization needle 3, before the cauterization. Here, it is desirable that the user carries out the check of at least half a rotation in order to thoroughly check the circumstances around the cauterization needle 3 (throughout the whole circumference around the cauterization needle 3).

II. For example, when the user determines that the check by the rotation of the cut surface B is completed, the user operates the cut surface C moving slider 57 to check the circumstances of the surrounding while moving the cut surface C in the center axis direction of the cauterization needle 3. Note that in place of the operation of the cut surface C moving slider 57, the trackball 51 and the confirmation key 52 or the mouse 6 may be used to move the cursor bar CSB by the cursor CS to move the cut surface C. Here, it is desirable that the user carries out the check of one stroke in the center axis direction of the cauterization needle 3 in order to thoroughly check the cauterization range. In this way, the user sufficiently cauterizes the target area while checking the circumstances around the cauterization needle 3 by the operation of the cut surface B rotary knob 56 and the circumstances in the center axis direction of the cauterization needle 3 by the operation of the cut surface C moving slider 57.

III. For example, when the user determines that the treatment is not completed yet, the user operates the energization button 58 on the control panel 5 or an energization menu on the monitor 4 in order to energize the cauterization needle 3 to cauterize the target area.

IV. On the other hand, when the user determines that the treatment is completed, the user operates the end button 59 on the control panel 5 or an end menu on the monitor 4 to end the entire process. Note that the end menu and the energization menu are displayed on the monitor 4 although not shown, or the end menu and the energization menu are operated by the mouse 6 or the trackball 51 and the confirmation key 52.

Figure 8B:
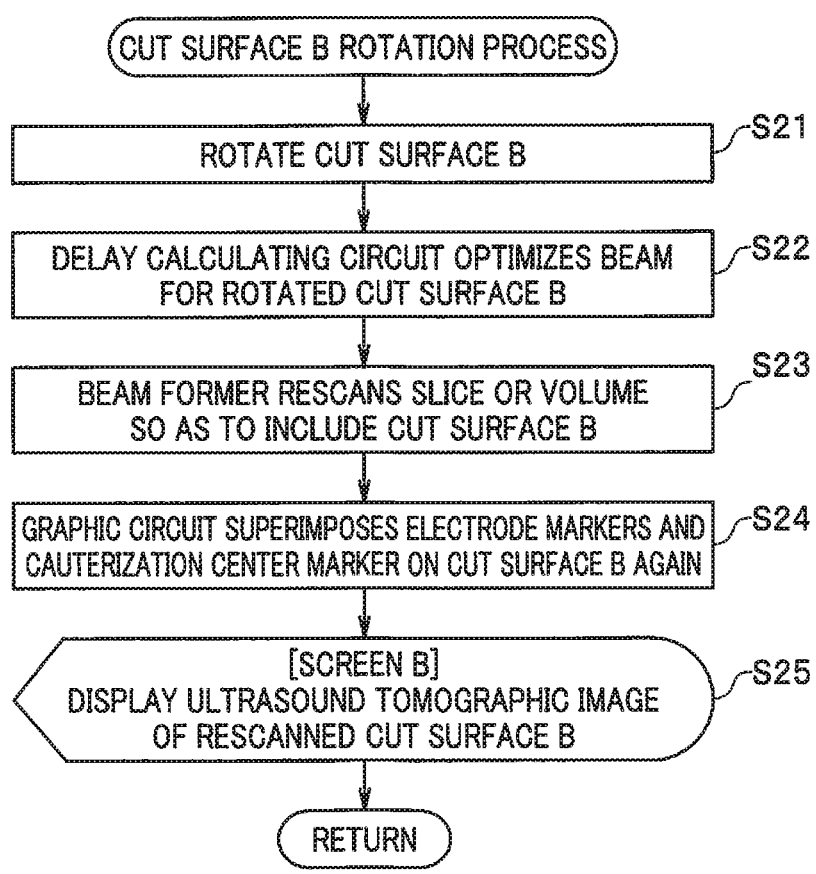
FIG. 8B is a flowchart showing details of a cut surface B rotation process in step S14 of FIG. 8A in the first embodiment.

Next, the CPU 29 determines whether the input in step S12 is input from the cut surface B rotary knob 56 (step S13). Here, if it is determined that the input is from the cut surface B rotary knob 56, a cut surface B rotation process as described later with reference to FIG. 8B is carried out (step S14).

Figure 8C:
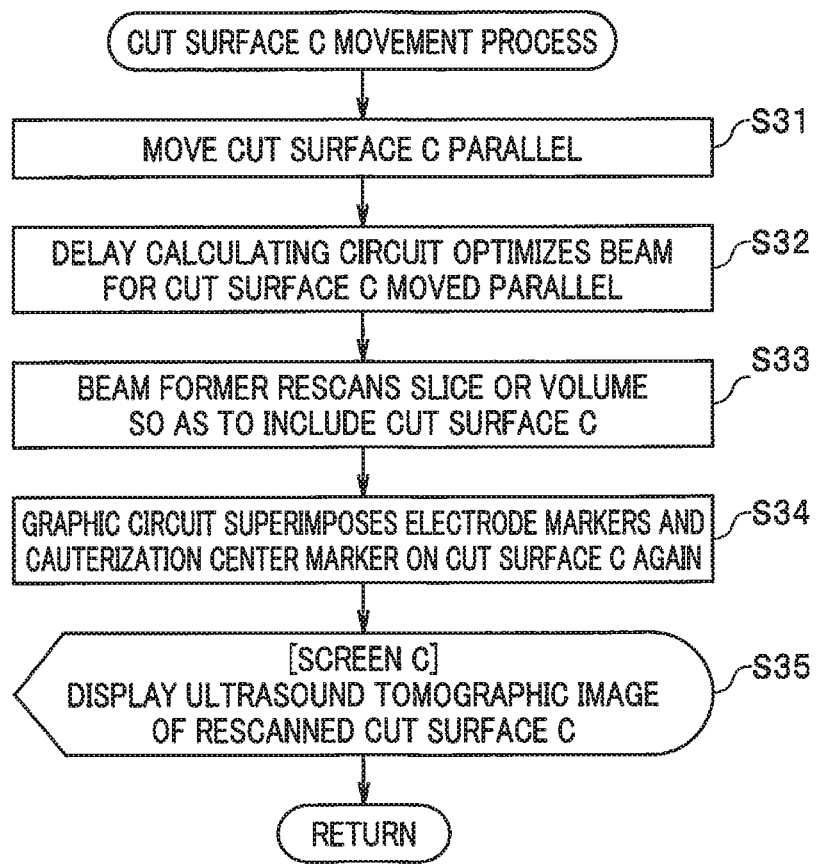
FIG. 8C is a flowchart showing details of a cut surface C movement process in step S16 of FIG. 8A in the first embodiment.

If it is determined that the input is not from the cut surface B rotary knob 56 in step S13, the CPU 29 determines whether the input in step S12 is input from the cut surface C moving slider 57 (step S15). Here, if it is determined that the input is from the cut surface C moving slider 57, a cut surface C movement process as described later with reference to FIG. 8C is carried out (step S16).

If it is determined that the input is not from the cut surface C moving slider 57 in step S15, the CPU 29 determines whether the input in step S12 is input from the energization button 58 or the energization menu (step S17). Here, if it is determined that the input is from the energization button 58 or the energization menu, the cauterization needle 3 is energized to cauterize the target area (step S18).

If it is determined that the input is not from the energization button 58 or the energization menu in step S17, the CPU 29 determines whether the input in step S12 is input from the end button 59 or the end menu (step S19). Here, if it is determined that the input is not from the end button 59 or the end menu, the CPU 29 goes to step S12 described above to wait for input operation from the user. On the other hand, if it is determined that the input is from the end button 59 or the end menu, the CPU 29 ends the entire process.

In this way, the user can return to step S12 to check the ultrasound slice image by changing the cut surface B and the cut surface C until it is determined that the cauterization is completed in step S19. Therefore, the user can check the change in the cauterization state while performing the cauterization of step S18. Furthermore, the state of the area of interest of the subject after the cauterization can be checked, for example. In this case, the process may be executed again from the volume scan of step S1 after the completion of the cauterization if necessary. If the user can determine that the cauterization is completed in step S19, the user can arbitrarily end the process.

Next, FIG. 8B is a flowchart showing details of the cut surface B rotation process in step S14 of FIG. 8A.

The CPU 29 sets the angle τ of the cut surface B (see FIGS. 3 and 9) based on the rotation inputted value inputted from the cut surface B rotary knob 56 in step S12 (step S21). In this way, the cut surface (here, the cut surface B) can be rotated around the straight line (here, the center axis of the cauterization needle 3) set by the straight line setting section in the three-dimensional space to set a new cut surface. Then, the CPU 29 calculates information of the center position vector and the normal vector of the cut surface B at the set angle τ and transmits the information to the delay calculating circuit 24.

Consequently, the delay calculating circuit 24 calculates the amount of delay of each ultrasound vibration element so as to optimize the ultrasound beam UB for the cut surface B at the set angle τ (step S22).

The beam former 23 receives the amount of delay from the delay calculating circuit 24 to perform rescanning and acquires one ultrasound slice image coinciding with the cut surface B by slice scan or acquires a plurality of ultrasound slice images including the cut surface B by volume scan (step S23). In this way, the rescanning can be performed by the volume scan or the slice scan as long as the ultrasound beam is optimal on the cut surface (same applies to rescanning of the cut surface C described below).

The graphic circuit 27 generates image data by superimposing the electrode markers 31 and 32, the cauterization center marker 30, and the cursor bar CSB on the ultrasound slice image of the cut surface B with a high spatial resolution acquired by the rescanning (step S24). The graphic circuit 27 displays the image data on the monitor 4 as shown in FIG. 4 (step S25) and returns to the process shown in FIG. 8A. Note that the cursor bar CSB is at the position C1 of FIG. 4 when the process of step S24 is first executed.

FIG. 8C is a flowchart showing details of the cut surface C movement process in step S16 of FIG. 8A.

The CPU 29 sets the amount of movement L of the cut surface C (see FIG. 4) based on the inputted value inputted from the cut surface C moving slider 57 in step S12 (step S31).

Next, the CPU 29 transmits the information of the center position vector and the normal vector of the cut surface C with the set amount of movement L to the delay calculating circuit 24, and the delay calculating circuit 24 calculates the amount of delay of each ultrasound vibration element so as to optimize the ultrasound beam UB for the cut surface C with the set amount of movement L (step S32).

The beam former 23 receives the amount of delay from the delay calculating circuit 24 to perform rescanning and acquires one ultrasound slice image coinciding with the cut surface C by slice scan or acquires a plurality of ultrasound slice images including the cut surface C by volume scan (step S33).

The graphic circuit 27 generates image data by superimposing a marker ME (see FIG. 5) corresponding to the electrode markers 31 and 32 or a marker MO (see FIG. 7) corresponding to the cauterization center marker 30 on the ultrasound slice image of the cut surface C with a high spatial resolution acquired by the rescanning (step S34). The graphic circuit 27 displays the image data on the monitor 4 (step S35) and returns to the process shown in FIG. 8A.

Here, the cut surface C is a surface perpendicular to the cauterization needle 3. Therefore, a marker corresponding to one of the electrode marker 31, the electrode marker 32, and the cauterization center marker 30 is rendered, or a marker corresponding to the markers is not rendered. That is, when the cut surface C intersects with one of a sphere with a predetermined radius δr around the electrode marker 31, a sphere with the predetermined radius δr around the electrode marker 32, and a sphere with the predetermined radius δr around the cauterization center marker 30, a marker at the center of the intersecting sphere with the radius δr is displayed. When the cut surface C does not intersect with any of the spheres, the marker is not displayed. This δr is a very small predetermined value.

FIG. 5 is a diagram showing an example of the ultrasound slice image of the cut surface C1 displayed on the monitor 4, FIG. 6 is a diagram showing an example of the ultrasound slice image of the cut surface C2 displayed on the monitor 4, and FIG. 7 is a diagram showing an example of the ultrasound slice image of the cut surface C3 displayed on the monitor 4.

When the cut surface C is the cut surface C1 intersecting with the sphere with the predetermined radius δr around the electrode marker 31, the marker ME like "+" corresponding to the electrode marker 31 is displayed on the screen C as shown in FIG. 5, for example. Note that when the cut surface C intersects with the sphere with the predetermined radius δr around the electrode marker 32, the marker ME is also displayed on the screen C as in FIG. 5.

When the cut surface C is the cut surface C2 between the electrode marker 31 and the cauterization center marker 30 and not intersecting with any of the spheres with the radius δr, the marker is not displayed on the screen C as shown in FIG. 6. Note that when the cut surface C is on the distal end side of the electrode marker 31, between the cauterization center marker 30 and the electrode marker 32, or on the proximal end side of the electrode marker 32 and not intersecting with the spheres with the radius δr, the marker is not displayed on the screen C as in FIG. 6.

Furthermore, when the cut surface C is the cut surface C3 intersecting with the sphere with the predetermined radius δr around the cauterization center marker 30, the marker MO like "X" corresponding to the electrode marker 31 is displayed on the screen C as shown in FIG. 7, for example.

Next, the optimization of the ultrasound beam UB for the cut surfaces B and C in the present embodiment will be described with reference to FIGS. 9 to 14. Note that the description of arrows indicating vectors and bold faces indicating vectors or matrices will be omitted in the present descriptive text for the convenience of character notation, and the vectors or the matrices will be specified as necessary.

Hereinafter, (1), (2-1) to (2-3), and (3-1) to (3-3) are related to derivation of relational expressions for optimizing the ultrasound beam UB, and (2-4) and (3-4) are related to action of the ultrasound diagnostic apparatus. In addition, (4-1) to (4-6) are related to modifications.

Furthermore, (2-1) to (2-4) below are related to the generation of the ultrasound beam UB for focusing at the arbitrary point P on the cut surface B (for putting the arbitrary point P into the focal area).

In addition, (3-1) to (3-4) below are related to the generation of the ultrasound beam UB for focusing at an arbitrary point Q on the cut surface C (for putting the arbitrary point Q into the focal area).

Note that although a plurality of coordinate systems are indicated in the following description, a "position vector" of a target point denotes a vector from the origin O in the coordinate system O-xyz to the target point.

(1) Relationship Between Ultrasound Vibration Element Array Surface 12a and Electrode Positions $E_1$ and $E_2$ (Corresponding to One and the Other of the Electrode Markers 31 and 32) on Cut Surface B FIG. 9 is a diagram showing a positional relationship between the ultrasound vibration element array surface 12a and the cut surface B.

As described, the coordinate system O-xyz is set as the orthonormal coordinate system of the right-hand system fixed to the ultrasound vibration element array surface 12a. That is, as described above, the origin O is set as the center of the ultrasound vibration element array surface 12a, the axis through the origin O and perpendicular to the ultrasound vibration element array surface 12a is defined as the z axis, the axis through the origin O and parallel to the insertion axis direction of the insertion portion of the ultrasound endoscope 1 is defined as the y axis, and the axis through the origin O and perpendicular to the z axis and the y axis is defined as the x axis. Therefore, if the ultrasound vibration element array surface 12a is arranged downward such that the xy plane is a horizontal plane for example, a normal direction of the z axis is perpendicularly downward (see FIG. 10).

An orthonormal basis in the x axis direction in the orthonormal coordinate system O-xyz can be expressed by a vector i, an orthonormal basis in the y axis direction can be expressed by a vector j, and an orthonormal basis in the z axis direction can be expressed by a vector k.

When the cut surface A selection slider 55 designates the cut surface A, the angle $\phi_y$ shown in FIG. 10 is inputted to the ultrasound observation apparatus 2. Here, FIG. 10 is a diagram showing a positional relationship between the ultrasound vibration element array surface 12a and the cut surface A.

Vectors i', j, and k' will be defined as vectors obtained by rotating the vectors i, j, and k by the angle $\psi_y$ around the y axis, respectively. In this case, a rotation matrix $T_y(\psi_y)$ of the angle $\psi_y$ around the y axis as shown in equation 8 can be used to obtain the vectors i', j, and from the vectors i, j, and k based on equation 7.

$$[i' \ j \ k'] = [i \ j \ k] T_y(\psi_y) \quad \text{[Equation 7]}$$

$$T_y(\psi_y) = \begin{pmatrix} \cos\psi_y & 0 & \sin\psi_y \\ 0 & 1 & 0 \\ -\sin\psi_y & 0 & \cos\psi_y \end{pmatrix} \quad \text{[Equation 8]}$$

Figure 11:
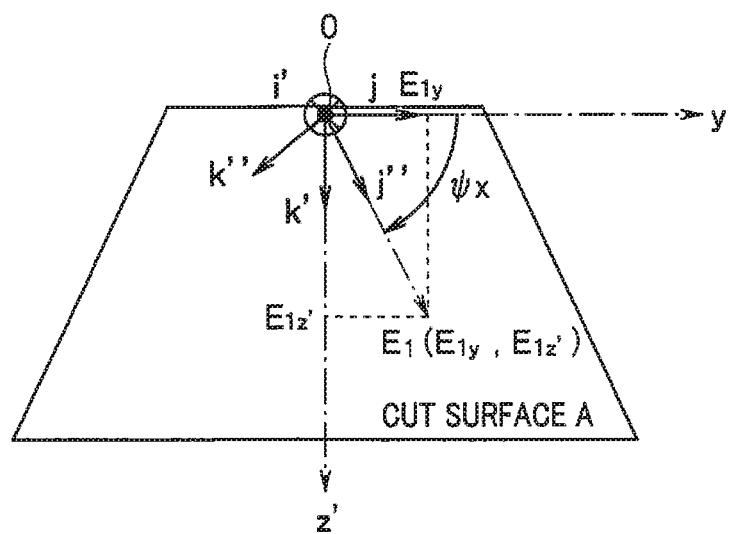
FIG. 11 is a diagram showing rotation of an orthonormal basis on the cut surface A according to the first embodiment.

An orthonormal coordinate system expressed by orthonormal bases of the obtained vectors i', j, and k' will be defined as O-x'yz'. In this case, when the trackball 51 and the confirmation key 52 are used to designate one electrode of the two electrodes provided on the cauterization needle 3 on the cut surface A, coordinates ($E_{1y}$, $E_{1z'}$) of a first electrode position $E_1$ on the cut surface A are determined as shown in FIG. 11. Here, FIG. 11 is a diagram showing rotation of the orthonormal bases on the cut surface A. Note that the first electrode position $E_1$ is also illustrated in FIG. 9 as a position on the cut surface B.

In this case, a value of $|OE_1|$ is obtained as shown in equation 9, and a value of an angle $\psi_x$ formed by the y axis and $OE_1$ is obtained as shown in equation 10.

$$|OE_1| = \sqrt{E_{1y}^2 + E_{1z'}^2} \qquad \text{[Equation 9]}$$

$$\psi_x = \tan^{-1}\frac{E_{1z'}}{E_{1y}} \qquad \text{[Equation 10]}$$

Furthermore, vectors i', j", and k" will be defined as vectors obtained by rotating the vectors i', j, and k' by the angle $\psi_x$ around an x' axis, respectively. In this case, following equations 11 and 12 can be used to obtain the vectors i', j", and k" from the vectors i', j, and k'. Here, $T_x(\psi_x)$ of equation 12 is a rotation matrix of the angle $\psi_x$ around the x' axis.

$$[\,i'\ \ j''\ \ k''\,] = [\,i'\ \ j\ \ k'\,]T_x(\psi_x) \qquad \text{[Equation 11]}$$

$$T_x(\psi_x) = \begin{pmatrix} 1 & 0 & 0 \\ 0 & \cos\psi_x & -\sin\psi_x \\ 0 & \sin\psi_x & \cos\psi_x \end{pmatrix} \qquad \text{[Equation 12]}$$

Furthermore, following equation 13 is established from j", $OE_1$, and $|OE_1|$.

$$j'' = \frac{\overrightarrow{OE_1}}{|\overrightarrow{OE_1}|} \qquad \text{[Equation 13]}$$

Therefore, $OE_1$ can be obtained as shown in equation 14 from equations 13 and 9.

$$\overrightarrow{OE_1} = |\overrightarrow{OE_1}|j''\qquad \text{[Equation 14]}$$

$$= \left(\sqrt{E_{1y}^2 + E_{1z'}^2}\right)j''$$

Furthermore, the vector j" in equation 14 can be obtained as shown in following equation 15 from equations 11, 7, and 10.

$$[\,i'\ \ j''\ \ k''\,] = [\,i'\ \ j\ \ k'\,]T_x(\psi_x) \qquad \text{[Equation 15]}$$

$$= [\,i\ \ j\ \ k\,]T_y(\psi_y)T_x(\psi_x)$$

$$= [\,i\ \ j\ \ k\,]T_y(\psi_y)T_x\!\left(\tan^{-1}\frac{E_{1z'}}{E_{1y}}\right)$$

In this way, j" obtained from equation 15 can be used in equation 14 to obtain a relationship between the vectors i, j, and k and the position vector $OE_1$ of the first electrode position $E_1$ based on the angle $\psi_y$ that is an already-known amount and coordinates ($E_{1y}$, $E_{1z'}$) of a first electrode in the cut surface A. Furthermore, a relationship between the vectors i, j, and k and the position vector $OE_2$ of a second electrode position $E_2$ can be obtained as in equations 14 and 15 based on the angle $\psi_y$ that is an already-known amount and coordinates ($E_{2y}$, $E_{2z'}$) of a second electrode in the cut surface A.

(2-1) Derivation of Position Vector p (=Position Vector OP) of Arbitrary Point P on Cut Surface B As shown in FIG. 9, a coordinate system $E_1$-$X_PY_PZ_P$ is an orthonormal coordinate system fixed to the cut surface B. Here, a point orthogonal to an $X_P$ axis, a $Y_P$ axis, and a $Z_P$ axis is defined as the first electrode position $E_1$, an axis through the first electrode position $E_1$ and perpendicular to the cut surface B is defined as the $Z_P$ axis, an axis through the first electrode position $E_1$ and in which a direction of a vector $E_1E_2$ determined by two electrode positions is the normal direction is defined as the $Y_P$ axis, and an axis through the first electrode position $E_1$ and perpendicular to the $Z_P$ axis and the $Y_P$ axis is defined as the $X_P$ axis.

An orthonormal basis in the $X_P$ axis direction in the orthonormal coordinate system $E_1$-$X_PY_PZ_P$ will be expressed by a vector $i_B$, an orthonormal basis in the $Y_P$ axis direction will be expressed by a vector $j_B$ and an orthonormal basis in the $Z_P$ axis direction will be expressed by a vector $k_B$.

In this case, the position vector $OE_1$ and the position vector $OE_2$ already obtained as described above can be used to obtain the vector $j_B$ as shown in following equation 16.

$$j_B = \frac{\overrightarrow{E_1E_2}}{|\overrightarrow{E_1E_2}|} \qquad \text{[Equation 16]}$$

$$= \frac{\overrightarrow{OE_2} - \overrightarrow{OE_1}}{|\overrightarrow{OE_2} - \overrightarrow{OE_1}|}$$

For an arbitrary point P ($X_P$, $Y_P$) on the cut surface B, following relational expression is established from FIG. 9.

$$\overrightarrow{E_1P} = X_P i_B + Y_P j_B \qquad \text{[Equation 17]}$$

Here, when the cut surface B rotary knob 56 is operated, the cut surface B rotates around the $Y_P$ axis by the angle $\tau$ according to the operation. Therefore, the angle $\tau$ is defined such that $\tau=0$ when $OE_1 \times j_B$ is parallel to $i_B$. When $i_B$ with $\tau=0$ is defined as $i_{B0}$, that is, when a unit vector in a direction of $OE_1 \times j_B$ is defined as $i_{B0}$, $i_B$ is a vector obtained by rotating $i_{B0}$ by the angle $\tau$ around the $Y_P$ axis. Similarly, when $k_B$ with $\tau=0$ is defined as $k_{B0}$, $k_B$ is a vector obtained by rotating $k_{B0}$ by the angle $\tau$ around the $Y_P$ axis. Furthermore, $k_B$ can be defined from $i_B$ and $j_B$, and $k_{B0}$ can be defined from $i_{B0}$ and $j_B$. Therefore, orthonormal bases $i_B$ and $k_B$ as well as $i_{B0}$ and $k_{B0}$ are expressed by following equations 18 to 22.

$$i_{B0} = \frac{\overrightarrow{OE_1} \times j_B}{|\overrightarrow{OE_1} \times j_B|} \quad \text{[Equation 18]}$$

$$= \frac{\dfrac{\overrightarrow{OE_1} \times (\overrightarrow{OE_2} - \overrightarrow{OE_1})}{|\overrightarrow{OE_2} - \overrightarrow{OE_1}|}}{\left|\dfrac{\overrightarrow{OE_1} \times (\overrightarrow{OE_2} - \overrightarrow{OE_1})}{|\overrightarrow{OE_2} - \overrightarrow{OE_1}|}\right|}$$

$$= \frac{(\overrightarrow{OE_1} \times \overrightarrow{OE_2})}{|\overrightarrow{OE_1} \times \overrightarrow{OE_2}|}$$

$$k_{B0} \equiv i_{B0} \times j_B \quad \text{[Equation 19]}$$

$$= \left\{\frac{(\overrightarrow{OE_1} \times \overrightarrow{OE_2})}{|\overrightarrow{OE_1} \times \overrightarrow{OE_2}|}\right\} \times \left\{\frac{(\overrightarrow{OE_2} - \overrightarrow{OE_1})}{|\overrightarrow{OE_2} - \overrightarrow{OE_1}|}\right\}$$

$$= \frac{(\overrightarrow{OE_1} \times \overrightarrow{OE_2}) \times (\overrightarrow{OE_2} - \overrightarrow{OE_1})}{|\overrightarrow{OE_1} \times \overrightarrow{OE_2}| \cdot |\overrightarrow{OE_2} - \overrightarrow{OE_1}|}$$

$$= \frac{(\overrightarrow{OE_1} \times \overrightarrow{OE_2}) \times \overrightarrow{OE_2} - (\overrightarrow{OE_1} \times \overrightarrow{OE_2}) \times \overrightarrow{OE_1}}{|\overrightarrow{OE_1} \times \overrightarrow{OE_2}| \cdot |\overrightarrow{OE_2} - \overrightarrow{OE_1}|}$$

$$= \frac{-\overrightarrow{OE_2} \times (\overrightarrow{OE_1} \times \overrightarrow{OE_2}) - \overrightarrow{OE_1} \times (\overrightarrow{OE_2} \times \overrightarrow{OE_1})}{|\overrightarrow{OE_1} \times \overrightarrow{OE_2}| \cdot |\overrightarrow{OE_2} - \overrightarrow{OE_1}|}$$

$$= -\frac{\overrightarrow{OE_1} \times (\overrightarrow{OE_2} \times \overrightarrow{OE_1}) + \overrightarrow{OE_2} \times (\overrightarrow{OE_1} \times \overrightarrow{OE_2})}{|\overrightarrow{OE_1} \times \overrightarrow{OE_2}| \cdot |\overrightarrow{OE_2} - \overrightarrow{OE_1}|}$$

$$= -\frac{\overrightarrow{OE_2}|\overrightarrow{OE_1}|^2 - \overrightarrow{OE_1}(\overrightarrow{OE_1} \cdot \overrightarrow{OE_2}) + \overrightarrow{OE_1}|\overrightarrow{OE_2}|^2 - \overrightarrow{OE_2}(\overrightarrow{OE_1} \cdot \overrightarrow{OE_2})}{|\overrightarrow{OE_1} \times \overrightarrow{OE_2}| \cdot |\overrightarrow{OE_2} - \overrightarrow{OE_1}|}$$

$$= -\frac{\{|\overrightarrow{OE_2}|^2 - (\overrightarrow{OE_1} \cdot \overrightarrow{OE_2})\}\overrightarrow{OE_1} + \{|\overrightarrow{OE_1}|^2 - (\overrightarrow{OE_1} \cdot \overrightarrow{OE_2})\}\overrightarrow{OE_2}}{|\overrightarrow{OE_1} \times \overrightarrow{OE_2}| \cdot |\overrightarrow{OE_2} - \overrightarrow{OE_1}|}$$

$$k_B \equiv i_B \times j_B \quad \text{[Equation 20]}$$

$$T_y(\tau) = \begin{pmatrix} \cos\tau & 0 & \sin\tau \\ 0 & 1 & 0 \\ -\sin\tau & 0 & \cos\tau \end{pmatrix} \quad \text{[Equation 21]}$$

$$[\,i_B \quad j_B \quad k_B\,] = [\,i_{B0} \quad j_B \quad k_{B0}\,]T_y(\tau) \quad \text{[Equation 22]}$$

$$\therefore i_B = \cos\tau\, i_{B0} - \sin\tau\, k_{B0}$$

$$= \cos\tau \frac{(\overrightarrow{OE_1} \times \overrightarrow{OE_2})}{|\overrightarrow{OE_1} \times \overrightarrow{OE_2}|} + \frac{\sin\tau}{|\overrightarrow{OE_1} \times \overrightarrow{OE_2}| \cdot |\overrightarrow{OE_2} - \overrightarrow{OE_1}|} \left[\{|\overrightarrow{OE_2}|^2 - (\overrightarrow{OE_1} \cdot \overrightarrow{OE_2})\}\overrightarrow{OE_1} + \{|\overrightarrow{OE_1}|^2 - (\overrightarrow{OE_1} \cdot \overrightarrow{OE_2})\}\overrightarrow{OE_2}\right]$$

Here, a symbol "×" used in the computation of the vectors indicates an outer product. Equation 16 is used for transformation of equation 18, equations 16 and 18 are used for transformation of equation 19, and equations 18, 19, and 21 are used for transformation of equation 22. Furthermore, $T_y(\tau)$ of equation 21 is a rotation matrix of the angle $\tau$ around the $Y_P$ axis.

A vector $E_1P$ on the cut surface B is expressed as shown in following equation 23.

$$\overrightarrow{E_1P} = X_P i_B + Y_P j_B \quad \text{[Equation 23]}$$

Therefore, a position vector p from the origin O to the arbitrary point P ($X_P$, $Y_P$) is as shown in following equation 24 when equation 23 is used.

$$p = \overrightarrow{OE_1} + \overrightarrow{E_1P} \quad \text{[Equation 24]}$$

$$= \overrightarrow{OE_1} + X_P i_B + Y_P j_B$$

$$= \overrightarrow{OE_1} + X_P \left( \cos\tau \frac{(\overrightarrow{OE_1} \times \overrightarrow{OE_2})}{|\overrightarrow{OE_1} \times \overrightarrow{OE_2}|} + \frac{\sin\tau}{|\overrightarrow{OE_1} \times \overrightarrow{OE_2}| \cdot |\overrightarrow{OE_2} - \overrightarrow{OE_1}|} \cdot \left[ \{|\overrightarrow{OE_2}|^2 - (\overrightarrow{OE_1} \cdot \overrightarrow{OE_2})\}\overrightarrow{OE_1} + \{|\overrightarrow{OE_1}|^2 - (\overrightarrow{OE_1} \cdot \overrightarrow{OE_2})\}\overrightarrow{OE_2} \right] \right) +$$

$$Y_P \frac{\overrightarrow{OE_2} - \overrightarrow{OE_1}}{|\overrightarrow{OE_2} - \overrightarrow{OE_1}|}$$

As described, based on equations 14 and 15 related to the position vector $OE_1$ and similar equations related to the position vector $OE_2$, the relationship between the vectors i, j, and k and the position vectors of the electrode positions $E_1$ and $E_2$ are obtained from the angle $\psi_y$, the coordinates ($E_{1y}$, $E_{1z}$) of the first electrode, and the coordinates ($E_{2y}$, $E_{2z}$) of the second electrode that are already-known amounts.

Therefore, the position vector p is also obtained from equation 24 based on the vectors i, j, and k, the angle $\psi_y$, the angle $\tau$, the first electrode position $E_1$ ($E_{1y}$, $E_{1z}$), the second electrode position $E_2$ ($E_{2y}$, $E_{2z}$), and the variables ($X_P$, $Y_P$) that are already-known amounts.

(2-2) Derivation of θ (0°≤θ≤360°) and φ (0°≤φ≤90°) that are Angles of Sound Axis of Ultrasound Beam UB for Focusing at Arbitrary Point P on Cut Surface B (for Putting Arbitrary Point P into Focal Area)

Following equation 25 is established for the position vector p of the arbitrary point P.

$$p = (i \cdot p)i + (j \cdot p)j + (k \cdot p)k \quad \text{[Equation 25]}$$

For the angle φ, following equation 26 as well as equation 27 are established from FIG. 2.

$$k \cdot p = |p|\cos\phi \quad \text{[Equation 26]}$$

$$\phi = \cos^{-1}\frac{k \cdot p}{|p|} \quad \text{[Equation 27]}$$

$$(0° \leq \phi \leq 90°)$$

Here, the position vector p is obtained from equation 24 described above based on the vectors i, j, and k, the angle $\psi_y$, the angle $\tau$, the first electrode position $E_1$ ($E_{1y}$, $E_{1z}$), the second electrode position $E_2$ ($E_{2y}$, $E_{2z}$), and the variables ($X_P$, $Y_P$) that are already-known amounts.

Therefore, the angle φ (0°≤φ≤90°) is also uniquely obtained from equation 27 based on the vectors i, j, and k, the angle $\psi_y$, the angle $\tau$, the first electrode position $E_1$ ($E_{1y}$, $E_{1z}$), the second electrode position $E_2$ ($E_{2y}$, $E_{2z}$), and the variables ($X_P$, $Y_P$) that are already-known amounts.

Figure 12:
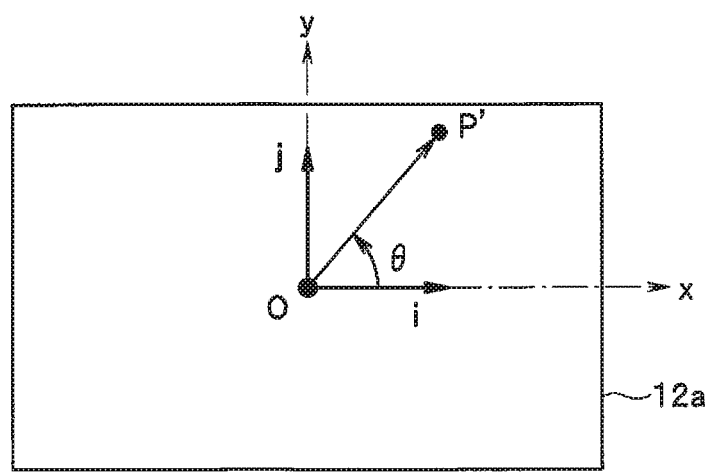
FIG. 12 is a diagram showing a position of a projection point P' to the ultrasound vibration element array surface of an arbitrary point P on the cut surface B according to the first embodiment.

For a projection point P' of the arbitrary point P to the ultrasound vibration element array surface 12a, following equations 28 to 30 are established from FIG. 12. Here, FIG. 12 is a diagram showing a position of the projection point P' of the arbitrary point P on the cut surface B to the ultrasound vibration element array surface.

$$\overrightarrow{OP'}=(i\cdot p)i+(j\cdot p)j \quad \text{[Equation 28]}$$

$$i\cdot\overrightarrow{OP'}=|\overrightarrow{OP'}|\cos\theta \quad \text{[Equation 29]}$$

$$j\cdot\overrightarrow{OP'}=|\overrightarrow{OP'}|\sin\theta \quad \text{[Equation 30]}$$

Based on equation 28, a size $|\overrightarrow{OP'}|$ of a position vector $\overrightarrow{OP'}$ is as shown in following equation 31.

$$|\overrightarrow{OP'}|=\sqrt{(i\cdot p)^2+(j\cdot p)^2} \quad \text{[Equation 31]}$$

Following equations 32 and 33 can be obtained from equations 28 to 31.

$$|\overrightarrow{OP'}|\cos\theta = i\cdot\overrightarrow{OP'} = i\cdot p \quad \text{[Equation 32]}$$
$$\therefore \cos\theta = \frac{i\cdot p}{|\overrightarrow{OP'}|} = \frac{i\cdot p}{\sqrt{(i\cdot p)^2+(j\cdot p)^2}}$$

$$|\overrightarrow{OP'}|\sin\theta = j\cdot\overrightarrow{OP'} = j\cdot p \quad \text{[Equation 33]}$$
$$\therefore \sin\theta = \frac{j\cdot p}{|\overrightarrow{OP'}|} = \frac{j\cdot p}{\sqrt{(i\cdot p)^2+(j\cdot p)^2}}$$

Here, the position vector p is obtained from equation 24 described above based on the vectors i, j, and k, the angle $\psi_y$, the angle $\tau$, the first electrode position $E_1$ ($E_{1y}$, $E_{1z}$), the second electrode position $E_2$ ($E_{2y}$, $E_{2z}$), and the variables ($X_P$, $Y_P$) that are already-known amounts.

Therefore, $\theta$ ($0 \leq \theta \leq 360°$) can also be uniquely obtained from equations 32 and 33 based on the vectors i, j, and k, the angle $\psi_y$, the angle $\tau$, the first electrode position $E_1$ ($E_{1y}$, $E_{1z}$), the second electrode position $E_2$ ($E_{2y}$, $E_{2z}$), and the variables ($X_P$, $Y_P$) that are already-known amounts.

Note that a reason that both of $\cos\theta$ and $\sin\theta$ are obtained in formulas for determining the angle $\theta$ in equations 32 and 33 is to determine in which one of first to fourth quadrants the angle $\theta$ is.

(2-3) Calculation of Amount of Delay $d_{st}$ for Generating Ultrasound Beam UB for Focusing at Arbitrary Point P on Cut Surface B (for Putting Arbitrary Point P into Focal Area)

Among the plurality of ultrasound vibration elements arranged in a matrix in the x direction and the y direction on the ultrasound vibration element array surface 12a, an ultrasound vibration element arranged at an s-th position in the x direction (vector i direction) and a t-th position in the y direction (vector j direction) will be written as A (s, t). Here, s and t can be positive or negative values including 0. Furthermore, an amount of delay of the ultrasound vibration element A (s, t) will be written as $d_{st}$.

As described in equation 3, in general, each amount of delay $d_{st}$ of the ultrasound vibration elements can be uniquely determined as shown in following equation 34, as the multivariable function f of the focal length $|p|$ from the origin O and the scan angles $\theta$ and $\phi$ of the ultrasound beam UB.

$$d_{st}=f_{st}(|p|,\theta,\phi) \quad \text{[Equation 34]}$$

Here, the focal length $|p|$ can be obtained from equation 24, the angle $\phi$ can be obtained from equation 27, and the angle $\theta$ can be obtained from equations 32 and 33, based on the vectors i, j, and k, the angle $\psi_y$, the angle $\tau$, the first electrode position $E_1$ ($E_{1y}$, $E_{1z}$), the second electrode position $E_2$ ($E_{2y}$, $E_{2z}$), and the variables ($X_P$, $Y_P$) that are already-known amounts. Therefore, the amount of delay $d_{st}$ is expressed as shown in following equation 35.

$$d_{st}=g_{st}(\psi_y,\tau,E_{1y},E_{1z},E_{2y},E_{2z},X_P,Y_P) \quad \text{[Equation 35]}$$

As a result, the amount of delay $d_{st}$ can be uniquely obtained by providing s and t in addition to the variables related to $|p|$.

(2-4) Action of Apparatus that Generates Ultrasound Beam UB for Focusing at Arbitrary Point P on Cut Surface B (for Putting Arbitrary Point P into Focal Area)

A small amount in the $X_P$ axis direction will be defined as $\delta X$, and a small amount in the $Y_P$ axis direction on the cut surface B will be defined as $\delta Y$. In this case, the delay calculating circuit 24 appropriately combines shifting the coordinates ($X_P$, $Y_P$) of the arbitrary point P by the small amount ($\delta X$, 0) and by the small amount (0, $\delta Y$) and repeatedly calculates the amount of delay of each ultrasound vibration element for each point obtained by evenly dividing the cut surface B by using equation 35.

Every time the delay calculating circuit 24 calculates the amount of delay, the beam former 23 generates a transmission drive signal and transmits the transmission drive signal to the ultrasound transducer 12. In this way, the ultrasound transducer 12 repeatedly transmits and receives the ultrasound beam UB for each point obtained by evenly dividing the cut surface B.

In this way, the transmission and reception are repeatedly performed, and the cut surface B is evenly rescanned by the optimized ultrasound beam UB.

(3-1) Derivation of Position Vector q (=Vector OQ) of Arbitrary Point Q on Cut Surface C A center $E_C$ of the cut surface C is on a center axis of the cauterization needle 3, that is, on a straight line $E_1E_2$. Therefore, if the amount of movement L that is an inputted value of the cut surface C moving slider 57 is defined as an amount of movement from the first electrode position $E_1$ with a unit of length $|E_1E_2|$, a position vector $OE_C$ is expressed as shown in following equation 36.

$$\overrightarrow{OE_C}=\overrightarrow{OE_1}+L\cdot\overrightarrow{E_1E_2} \quad \text{[Equation 36]}$$

Figure 13:
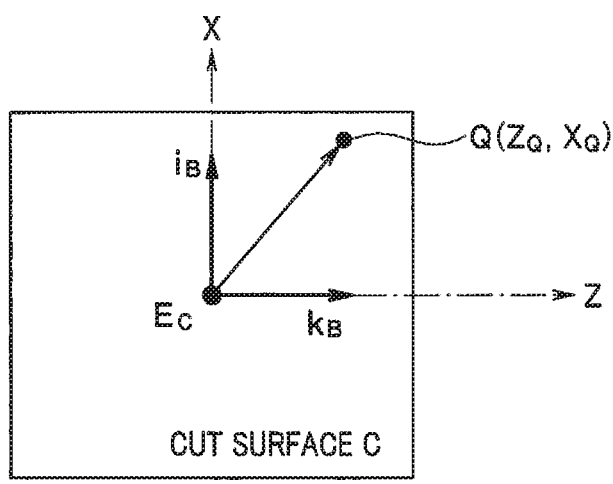
FIG. 13 is a diagram showing a position of an arbitrary point Q on the cut surface C according to the first embodiment.

The cut surface C is a surface perpendicular to the $Y_P$ axis of the cut surface B shown in FIG. 9, and the orthonormal basis of the cut surface C is provided by the vector $k_B$ and the vector $i_B$ as shown in FIG. 13 (this coordinate system is a ZX coordinate system in FIG. 13). Here, FIG. 13 is a diagram showing a position of the arbitrary point Q on the cut surface C. Therefore, if the coordinates of the arbitrary point Q on the cut surface C are defined as ($Z_Q$, $X_Q$), following equation 37 is established for the arbitrary point Q ($Z_Q$, $X_Q$) from FIG. 13.

$$\overrightarrow{E_CQ}=Z_Qk_B+X_Qi_B \quad \text{[Equation 37]}$$

Therefore, a position vector q of the arbitrary point Q ($X_Q$, $Y_Q$) is provided by following equation 38 by using equations 36 and 37.

$$q = \overrightarrow{OE_C} + \overrightarrow{E_CQ} \quad \text{[Equation 38]}$$
$$= \overrightarrow{OE_1} + L\cdot\overrightarrow{E_1E_2} + Z_Qk_B + X_Qj_B$$
$$= (1-L)\overrightarrow{OE_1} + L\cdot\overrightarrow{OE_2} + Z_Qk_B + X_Qj_B$$

Here, based on equations 16, 20, and 22 of (2-1), the relationship between the vectors i, j, and k and the vectors $j_B$ and $k_B$ is obtained from the position vectors $OE_1$ and $OE_2$ of the electrode positions $E_1$ and $E_2$ and the angle τ that is an already-known amount of inputted value. Furthermore, based on equations 14 and 15 related to the position vector $OE_1$ and similar equations related to the position vector $OE_2$, the relationship between the vectors i, j, and k and the position vectors of the electrode positions $E_1$ and $E_2$ is obtained from the angle $\psi_y$, the coordinates ($E_{1y}$, $E_{1z'}$) of the first electrode, and the coordinates ($E_{2y}$, $E_{2z'}$) of the second electrode that are already-known amounts.

Therefore, the position vector q can also be obtained from equation 38 based on the vectors i, j, and k, the angle $\psi_y$, the angle τ, the first electrode position $E_1$ ($E_{1y}$, $E_{1z'}$), the second electrode position $E_2$ ($E_{2y}$, $E_{2z'}$), and the variables ($Z_Q$, $X_Q$) that are already-known amounts.

(3-2) Derivation of θ (0°≤θ≤360°) and φ (0°≤φ'≤90°) that are Angles of Sound Axis of Ultrasound Beam UB for Focusing at Arbitrary Point Q on Cut Surface C (for Putting Arbitrary Point Q into Focal Area)

The angles θ' and φ' are derived as in (2-2) described above.

(3-3) Calculation of Amount of Delay $d_{st}'$ for Generating Ultrasound Beam UB for Focusing at Arbitrary Point Q on Cut Surface C (for Putting Arbitrary Point Q into Focal Area)

The amount of delay $d_{st}'$ can be calculated as in (2-3) described above.

(3-4) Action of Apparatus that Generates Ultrasound Beam UB for Focusing at Arbitrary Point Q on Cut Surface C (for Putting Arbitrary Point Q into Focal Area)

This is similar to (2-4) described above. That is, a small amount in the $X_Q$ axis direction will be defined as δX, and a small amount in the $Y_Q$ axis direction will be defined as δY on the cut surface C. In this case, the delay calculating circuit 24 appropriately combines shifting the coordinates ($X_Q$, $Y_Q$) of the arbitrary point Q by the small amount (δX, 0) and by the small amount (0, δY) and repeatedly calculates the amount of delay of each ultrasound vibration element for each point obtained by evenly dividing the cut surface C by using equation 35.

Every time the delay calculating circuit 24 calculates the amount of delay, the beam former 23 generates a transmission drive signal and transmits the transmission drive signal to the ultrasound transducer 12. In this way, the ultrasound transducer 12 repeatedly transmits and receives the ultrasound beam UB for each point obtained by evenly dividing the cut surface C.

In this way, the transmission and reception are repeatedly performed, and the cut surface C is evenly rescanned by the optimized ultrasound beam UB.

(4-1) Modification 1

The constants are used for the numbers of opening elements Δx and Δy in the description above. However, if the focal length |p| (in scanning on the cut surface B) or the focal length |q| (in scanning on the cut surface C) is smaller than a predetermined distance, convergence of the ultrasound beam UB is difficult, and the ultrasound beam UB becomes greater than an appropriate beam diameter (this tendency increases when the numbers of opening elements Δx and Δy that are constants are large).

Therefore, the beam former 23 may change the size (the numbers of opening elements: Δx, Δy) of the opening 12b used for actual excitation in the ultrasound vibration element array surface 12a according to the angle $\psi_y$, the angle τ, the amount of movement L, the first electrode position $E_1$ ($E_{1y}$, $E_{1z'}$), the second electrode position $E_2$ ($E_{2y}$, $E_{2z'}$), and the variables ($X_P$, $Y_P$) or the variables ($X_Q$, $Y_Q$).

For example, if the arbitrary point P is near the ultrasound transducer 12, and the focal length |p| is smaller than the predetermined distance, the numbers of opening elements Δx and Δy may be reduced according to the focal length |p|. If the focal length |p| is equal to or greater than the predetermined distance, the numbers of opening elements Δx and Δy may be certain values greater than when the numbers of opening elements Δx and Δy are smaller than the predetermined distance.

Figure 14:
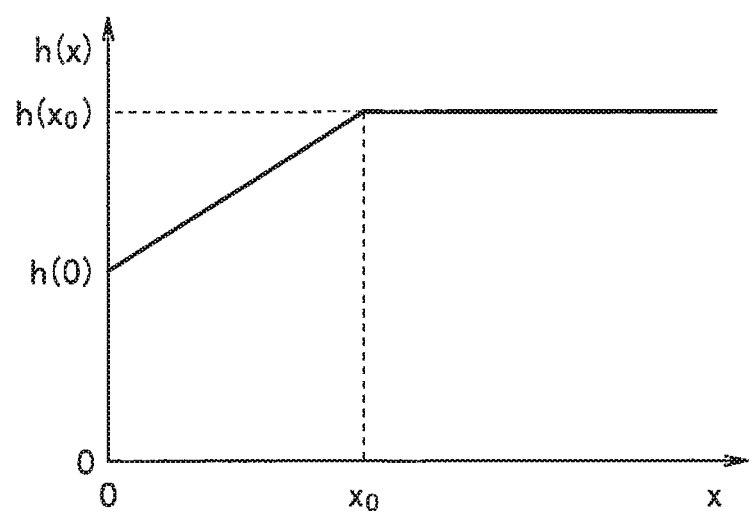
FIG. 14 is a diagram showing an example of a function shape in changing a size of an opening of the ultrasound vibration element array according to a focal length according to the first embodiment.

Here, FIG. 14 is a diagram showing an example of a function shape in changing the size of the opening of the ultrasound vibration element array according to the focal length.

A function h(x) with a variable x is a function that takes an initial value h(0) when x=0, monotonically increases when 0≤x<$x_0$, and takes a certain value h($x_0$) when $x_0$≤x.

For example, functions in a shape of the function h(x), specifically, $h_{Bx}$ for a function applied to Δx in rescanning the cut surface B, $h_{By}$ for a function applied to Δy in rescanning the cut surface B, $h_{Cx}$ for a function applied to Δx in rescanning the cut surface C, and $h_{Cy}$ for a function applied to Δy in rescanning the cut surface C, can be used to express Δx and Δy as shown in following equations 39 to 42.

$$\Delta x = h_{Bx}(\psi_y, \tau, E_{1y}, E_{1z'}, E_{2y}, E_{2z'}, X_P Y_P) \quad \text{[Equation 39]}$$

$$\Delta y = h_{By}(\psi_y, \tau, E_{1y}, E_{1z'}, E_{2y}, E_{2z'}, X_P Y_P) \quad \text{[Equation 40]}$$

$$\Delta x = h_{Cx}(\psi_y, \tau, E_{1y}, E_{1z'}, E_{2y}, E_{2z'}, X_P Y_P) \quad \text{[Equation 41]}$$

$$\Delta y = h_{Cy}(\psi_y, \tau, E_{1y}, E_{1z'}, E_{2y}, E_{2z'}, X_P Y_P) \quad \text{[Equation 42]}$$

(4-2) Modification 2

In (2-3) described above, the calculation method in which each amount of delay $d_{st}$ of the ultrasound vibration element A (s, t) in scanning the cut surface B can be uniquely determined as the multivariable function f of the focal length |p| and the scan angles θ and φ of the ultrasound beam UB, that is, a generally known calculating method shown in equation 34 (or equation 35), is used.

However, a calculating method using following equation 43 may be utilized based on a vector $A_{st}P$ from the ultrasound vibration element A (s, t) to the arbitrary point P, wherein c is a speed of sound.

$$d_{st} = \frac{|\overrightarrow{A_{st}P}|}{c} \quad \text{[Equation 43]}$$

Here, a following relational expression is established, wherein δx is an element pitch in the x axis direction of the ultrasound vibration elements, and δy is an element pitch in the y axis direction of the ultrasound vibration elements, as shown in FIG. 9.

$$\overrightarrow{OA_{st}} = (s \cdot \delta x)i + (t \cdot \delta y)j \quad \text{[Equation 44]}$$

This equation 44 and equation 24 described above can be used to express equation 43 as shown in following equation 45.

$$d_{st} = \frac{|\overrightarrow{A_{st}P}|}{c} \quad \text{[Equation 45]}$$

-continued $$= \frac{|\overrightarrow{OP} - \overrightarrow{OA_{st}}|}{c}$$

$$= \frac{|p - (s \cdot \delta x)i - (t \cdot \delta y)j|}{c}$$

$$= \frac{1}{c} \left| \overrightarrow{OE_1} + X_P \left( \begin{array}{c} \cos\tau \frac{(\overrightarrow{OE_1} \times \overrightarrow{OE_2})}{|\overrightarrow{OE_1} \times \overrightarrow{OE_2}|} + \\ \frac{\sin\tau}{|\overrightarrow{OE_1} \times \overrightarrow{OE_2}| \cdot |\overrightarrow{OE_2} - \overrightarrow{OE_1}|} \cdot \\ \left[ \{|\overrightarrow{OE_2}|^2 - (\overrightarrow{OE_1} \cdot \overrightarrow{OE_2})\}\overrightarrow{OE_1} + \\ \{|\overrightarrow{OE_1}|^2 - (\overrightarrow{OE_1} \cdot \overrightarrow{OE_2})\}\overrightarrow{OE_2} \right] \end{array} \right) + Y_P \frac{\overrightarrow{OE_2} - \overrightarrow{OE_1}}{|\overrightarrow{OE_2} - \overrightarrow{OE_1}|} - (s \cdot \delta x)i - (t \cdot \delta y)j \right|$$

Here, based on equations 14 and 15 related to the position vector $OE_1$ and similar equations related to the position vector $OE_2$, the relationship between the vectors i, j, and k and the position vectors of the electrode positions $E_1$ and $E_2$ are obtained from the angle $\psi_y$, the coordinates ($E_{1y}$, $E_{1z'}$) of the first electrode, and the coordinates ($E_{2y}$, $E_{2z'}$) of the second electrode that are already-known amounts.

Therefore, the amount of delay $d_{st}$ is also obtained from equation 45 based on the vectors i, j, and k, the angle $\psi_y$, the angle $\tau$, the first electrode position $E_1$ ($E_{1y}$, $E_{1z'}$), the second electrode position $E_2$ ($E_{2y}$, $E_{2z'}$), the element pitches ($\delta x$, $\delta y$), the variables ($X_P$, $Y_P$), and the variables (s, t) that are already-known amounts.

Each amount of delay $d_{st}$ of the ultrasound vibration element A (s, t) in scanning the cut surface C can also be obtained in a substantially same manner.

(4-3) Modification 3

Although the cut surface B to be rescanned is a surface including the cauterization needle 3 in (2-1) to (2-4) described above, the cut surface B may be an arbitrary surface.

(4-4) Modification 4

Although two electrode positions $E_1$ and $E_2$ and the angle $\psi_y$ are used (that is, two points and one direction are used) to set the cut surface to be rescanned, such as the cut surface B, in (2-1) to (2-4) described above, the setting method of the cut surface to be rescanned is not limited to this example. For example, a method of setting the cut surface to be rescanned by designating three points may be adopted, or a method of setting the cut surface to be rescanned by designating one point and two directions may be used.

(4-5) Modification 5

Although the cut surface B to be rescanned is a plane in (2-1) to (2-4) described above, the cut surface B may be a curved surface.

(4-6) Modification 6

Although the ultrasound vibration element array surface 12a has a two-dimensional planar shape in the example described above, the shape is not limited to this. For example, a surface with a convex curved shape may be used as described in FIG. 7, 10, or 12 of Japanese Patent No. 4488288 (Japanese Patent Application Laid-Open Publication No. 2005-168768). In this case, there is an advantage that the angle of view is wide, and the scan range is wide.

(4-7) Modification 7

In step S6 described above, the cauterization needle 3 is rendered on the ultrasound slice image of the cut surface A along the center axis of the cauterization needle 3, and the user designates the electrode position of the cauterization needle 3 in this state. However, the cauterization needle 3 may be a needle that tends to be bent, and the angle of projection from the forceps channel 13 may be slightly different from an initial design value. The cauterization needle 3 may be bent during puncture or cauterization of the target area of the tissue due to a reason that the target area is hard or due to other reasons, and the entire image of the cauterization needle 3 may not be depicted in the ultrasound slice image of one cut surface. Furthermore, when the cauterization needle 3 is bipolar, the bright points that are images of two electrodes may not be rendered at the same time on the cut surface A. In such a case, following operation may be performed.

The user operates the cut surface A selection slider 55 to find a cut surface in which each bright point is rendered.

The user operates the trackball 51, the confirmation key 52, and the mouse 6 as a straight line setting section and designates each electrode position on separate cut surfaces.

The graphic circuit 27 superimposes and displays the electrode marker 31 on the distal end side or the electrode marker 32 on the proximal end side on the ultrasound slice image of the cut surface rendering each bright point (as in step S8).

The graphic circuit 27 changes the direction of the cut surface B such that the cut surface B includes the straight line passing through two electrode positions and that the normal line of the cut surface B is parallel to a cut surface A' (not shown) in which the electrode marker 31 on the distal end side is designated.

The graphic circuit 27 changes the position and the direction of the cut surface C such that the cut surface C is perpendicular to the straight line passing through two electrode positions and that the upper direction of the cut surface C is parallel to the cut surface A'.

The graphic circuit 27 further moves parallel and changes the position of the cut surface C such that the center of the cut surface C coincides with the electrode position on the distal end side (as in step S8).

The graphic circuit 27 also superimposes the electrode marker 31 and the electrode marker 32 on the proximal end side on the ultrasound slice image of the screen B and displays the image on the monitor 4 (as in step S9).

As a result of the operation, the entire image of the cauterization needle 3 is not rendered on the cut surface A', but the entire image is rendered on the cut surface B created again. Therefore, cauterization can be performed, and the treatment effect can be determined, while the entire image is viewed.

Note that although the origin O shown in FIG. 2 and the like is the center of the ultrasound vibration element array surface 12a of the ultrasound transducer 12 in the description above, the origin O may be a position that is not the center.

According to the first embodiment, the scan is performed again (rescan) by changing the scan conditions set by the scan condition setting section according to the set cut surface, and the ultrasound slice image of the set cut surface is generated based on the ultrasound data acquired in the rescan. Therefore, the spatial resolution of the ultrasound slice image corresponding to the cut surface intersecting with the sound axis can be improved. As a result, even if the cut surface B or the cut surface C is changed and newly set, the rescan is performed with the optimized ultrasound beam UB, and the ultrasound slice image of the cut surface B or the cut surface C with a high spatial resolution can be observed.

Since the scan conditions are changed to include the amount of delay regarding the drive timing of the ultrasound vibration elements, the ultrasound slice image with an improved spatial resolution can be acquired just by changing the amount of delay calculated by the delay calculating circuit 24.

In this case, an appropriate amount of delay according to the direction of the cut surface can be set by setting the amount of delay based on the direction of the cut surface as viewed from the ultrasound transducer. An appropriate amount of delay according to the distance to the cut surface can be set by setting the amount of delay based on the distance from the ultrasound transducer to the cut surface. In this case, the distance to the cut surface can be further indicated by the focal length of the ultrasound or the focal depth of the ultrasound to use the distance information suitable for the setting of the ultrasound beam.

Furthermore, the amount of delay can be set so as to scan each point obtained by evenly dividing the cut surface, and an ultrasound slice image can be obtained in which the resolution corresponding to the cut surface is more homogeneous than in the past.

When the scan conditions are changed to include the conditions of the arrangement range of the ultrasound vibration elements regarding the transmission or reception of the ultrasound, the beam diameter of the ultrasound beam UB at the focal position can be appropriately maintained.

Further, when a plurality of points or a point and a direction are designated on the ultrasound slice image of the cut surface to set a straight line to set a new cut surface by rotating the cut surface around the set straight line, a cut surface including a treatment instrument, such as the cauterization needle 3, can be easily set. The existence of blood vessels or other organs around the treatment instrument that should not be damaged can be checked before the treatment, and a sufficient margin from the treatment range can be surely reserved.

In addition, based on the coordinates of a plurality of points designated on the ultrasound slice image of the cut surface, a marker is provided after calculating a new point, and the marker is superimposed on the ultrasound slice image of the cut surface. Therefore, the cauterization center of the bipolar cauterization needle 3 can be displayed as a cauterization center marker to easily check the cauterization center, for example. In this way, whether the cauterization treatment is applied to the region to be treated in the area of interest can be easily checked, for example.

When the rescan is performed by volume scan, slice scan needs to be performed for a plurality of times while performing multi-focusing, and the real-time property is reduced. However, when the rescan is performed only by slice scan, the frame rate can be improved (for example, multiple times larger than in the volume scan) to improve the real-time property.

According to the first embodiment, the input circuit 25, the CPU 29, the beam former 23, the delay calculating circuit 24, and the graphic circuit 27 wait for operation of the cut surface B rotary knob 56 and the cut surface C moving slider 57 by the user and immediately acts when there is operation. Therefore, when the user rotates the cut surface B or moves the cut surface C parallel, rescanning is immediately carried out for the changed cut surface. As a result, when the user changes the cut surface, the user can immediately observe an excellent ultrasound slice image scanned under appropriate scan conditions according to the change. Particularly, an ultrasound slice image with a homogeneous resolution without unevenness can be automatically and simply observed immediately after the change in the cut surface, without extra image adjustment. This is significantly convenient for the user in busy situations, such as during cauterization treatment.

[Notes]

According to the embodiment of the present invention, following configurations can be obtained. Or, the following configurations may be further incorporated into the embodiment of the present invention.

(1) An ultrasound diagnostic apparatus including:

a scanning section that generates an ultrasound beam by driving an ultrasound transducer including two-dimensionally arranged ultrasound vibration elements and acquires ultrasound data of a three-dimensional space from an echo obtained by scanning with the ultrasound beam in the three-dimensional space;

a scan condition setting section that sets conditions of the ultrasound beam; and a slice image generating section that generates an ultrasound slice image in a surface in the three-dimensional space, wherein the ultrasound diagnostic apparatus further includes a cut surface setting section that sets a cut surface for the three-dimensional space after the ultrasound data is acquired, the scan condition setting section changes the conditions of the ultrasound scan according to the cut surface set by the cut surface setting section, the scanning section acquires new ultrasound data by scanning with the ultrasound beam in the three-dimensional space and/or in the cut surface under the conditions changed by the scan condition setting section, and the slice image generating section generates a new ultrasound slice image from the new ultrasound data acquired by the scanning section.

(2) The ultrasound diagnostic apparatus according to note 1, wherein the conditions set by the scan condition setting section include a focal depth or a focal length of the ultrasound beam.

(3) The ultrasound diagnostic apparatus according to note 1, wherein the conditions set by the scan condition setting section include the number of focuses of the ultrasound beam.

(4) The ultrasound diagnostic apparatus according to note 1, wherein the conditions set by the scan condition setting section include a condition related to an opening of the ultrasound beam.

(5) The ultrasound diagnostic apparatus according to note 4, wherein the condition related to the opening of the ultrasound beam includes one of a transmission opening dimension, a reception opening dimension, the number of transmission elements, and the number of reception elements.

(6) The ultrasound diagnostic apparatus according to note 1, wherein the conditions set by the scan condition setting section include a condition related to a frequency filter for an ultrasound echo.

(7) The ultrasound diagnostic apparatus according to note 1, wherein the conditions set by the scan condition setting section include a condition related to STC for the ultrasound echo.

(8) The ultrasound diagnostic apparatus according to note 1, further including:
a Doppler processing section that renders a blood stream based on a Doppler effect; and
a Doppler scan condition setting section that sets Doppler scan conditions of the Doppler processing section, wherein
the Doppler scan condition setting section changes the conditions of Doppler scan according to the cut surface set by the cut surface setting section,
the scanning section acquires new ultrasound Doppler data by scanning with the ultrasound beam in the three-dimensional space and/or in the cut surface under the conditions changed by the Doppler scan condition setting section, and
the slice image generating section superimposes new ultrasound Doppler data on the ultrasound slice image from the new ultrasound Doppler data acquired by the scanning section.
(9) The ultrasound diagnostic apparatus according to note 8, wherein
the conditions set by the Doppler scan condition setting section include a repetition frequency of the Doppler scan.
(10) The ultrasound diagnostic apparatus according to note 1, wherein
the conditions set by the scan condition setting section vary with a direction of a sound axis of the ultrasound beam for the scan by the scanning section.
(11) The ultrasound diagnostic apparatus according to note 10, wherein
when the cut surface set by the cut surface setting section is oblique to a center axis of an arrangement surface of the ultrasound vibration elements in the ultrasound transducer, at least one of the focal depth, the focal length, the number of focuses, the transmission opening dimension, the reception opening dimension, the number of transmission elements, the number of reception elements, the frequency filter, and the STC set by the scan condition setting section and the repetition frequency of the Doppler scan set by the Doppler scan condition setting section varies with the direction of the sound axis of the ultrasound beam for the scan by the scanning section.
(12) The ultrasound diagnostic apparatus according to note 1, wherein
the cut surface setting section sets a position and a direction of the cut surface to set the cut surface.
(13) The ultrasound diagnostic apparatus according to note 1, wherein
the cut surface setting section includes a straight line setting section that sets a straight line by designating a plurality of points or a point and a direction on the ultrasound slice image in the three-dimensional space generated by the slice image generating section, and
the cut surface setting section sets the cut surface such that the cut surface can be changed by rotating the cut surface around the straight line set by the straight line setting section.
(14) The ultrasound diagnostic apparatus according to note 1, wherein
the cut surface setting section includes a straight line setting section that sets a straight line by designating a plurality of points or a point and a direction on the ultrasound slice image in the three-dimensional space generated by the slice image generating section, and
the cut surface setting section sets a surface perpendicular to the straight line set by the straight line setting section as the cut surface.
(15) The ultrasound diagnostic apparatus according to note 14, wherein
the cut surface setting section sets the cut surface perpendicular to the straight line set by the straight line setting section such that the cut surface can be moved parallel along the straight line.
(16) The ultrasound diagnostic apparatus according to note 1, wherein
the cut surface setting section includes a designation section that designates a plurality of points on the ultrasound slice image in the three-dimensional space generated by the slice image generating section, and
the ultrasound diagnostic apparatus further includes:
a calculating unit that calculates a new point calculated from coordinates of the plurality of points; and
a marker superimposing section that provides a marker to the new point and superimposes the marker on the ultrasound slice image in the three-dimensional space generated by the slice image generating section.
(17) The ultrasound diagnostic apparatus according to note 16, wherein
the cut surface setting section sets a cut surface perpendicular to a straight line passing through the plurality of points designated by the designation section such that the cut surface can be moved parallel along the straight line,
the slice image generating section newly generates an ultrasound slice image of the cut surface, and
the marker superimposing section further superimposes the marker on a position corresponding to the new point calculated by the calculating unit, on the ultrasound slice image of the cut surface newly generated by the slice image generating section.
(18) The ultrasound diagnostic apparatus according to note 16, wherein
the calculating unit sets a middle point of two points of the plurality of points as the new point.
(19) The ultrasound diagnostic apparatus according to any one of notes 16 to 18, wherein
the plurality of points designated by the designation section correspond to positions of electrodes provided on a puncture needle that is used in combination, and
the new point calculated by the calculating unit corresponds to a center of an area of cauterization using the electrodes.

Note that although the ultrasound diagnostic apparatus is mainly described above, an operation method of operating the ultrasound diagnostic apparatus as described above may be adopted. A control program for a computer to perform control of operating the ultrasound diagnostic apparatus as described above, a computer-readable non-transitory recording medium recording the control program, or the like may also be adopted.

The present invention is not limited to the embodiment, and in an execution phase, the constituent elements can be modified without departing from the concept of the present invention to embody the present invention. In addition, various aspects of invention can be formed by appropriately combining a plurality of constituent elements disclosed in the embodiment. For example, some constituent elements of all constituent elements illustrated in the embodiment may be deleted. Furthermore, constituent elements across different embodiments may be appropriately combined. In this way, it is obvious that various modifications and applications are possible without departing from the scope of the invention.

What is claimed is:

1. An ultrasound diagnostic apparatus comprising:
an ultrasound transducer comprising two-dimensionally arranged ultrasound vibration elements; and
a processor comprising hardware, wherein the processor is configured to:
set scan conditions comprising an amount of delay related to drive timing of the ultrasound vibration elements;
drive the ultrasound transducer based on the scan conditions, to generate an ultrasound beam;
scan a plane by transmitting and receiving the ultrasound beam multiple times while changing the direction of the ultrasound beam; and
acquire an ultrasound slice image of the plane along a sound axis of the ultrasound beam, based on ultrasound data acquired by the scanning,
wherein the processor is configured to:
acquire a plurality of ultrasound slice images by scanning a plane multiple times in a three-dimensional space while changing the direction of the plane;
form three-dimensional volume data based on the plurality of the ultrasound slice images;
receive an instruction for setting a position of a cut surface, and set, based on the received set position of the cut surface, the cut surface at the position comprising a position of a surface intersecting with the sound axis;
generate a first ultrasound slice image of the cut surface from the three-dimensional volume data; and
determine a focal length of the ultrasound beam or a focal depth of the ultrasound beam, according to a distance from the ultrasound transducer to an arbitrary point on the cut surface, and
wherein the processor is configured to:
change the scan conditions comprising the amount of delay based on the determined focal length or focal depth;
drive the ultrasound transducer based on the changed scan conditions, to generate the ultrasound beam such that the arbitrary point enters a focal area;
rescan the cut surface by successively transmitting and receiving the ultrasound beam such that the arbitrary point enters the focal area, while moving a position of the arbitrary point from a position of a certain one point of a plurality of points evenly arranged on the cut surface to a position of another one point of the plurality of points; and
generate a second ultrasound slice image of the cut surface based on ultrasound data acquired by the rescanning, the second ultrasound slice image being different from the first ultrasound slice image.

2. The ultrasound diagnostic apparatus according to claim 1,
wherein the processor is configured to set the amount of delay based on a direction of the cut surface viewed from the ultrasound transducer.

3. The ultrasound diagnostic apparatus according to claim 1,
wherein the scan conditions changed by the processor comprises: a condition of an arrangement range of the ultrasound vibration elements related to the transmitting or the receiving of the ultrasound beam, of the ultrasound vibration elements two-dimensionally arranged on the ultrasound transducer.

4. The ultrasound diagnostic apparatus according to claim 1,
wherein the processor is configured to set a straight line by designating a plurality of points or a point and a direction on the first ultrasound slice image and rotate the cut surface around the straight line to set the cut surface that is new in the three-dimensional space.

5. The ultrasound diagnostic apparatus according to claim 1,
wherein the processor is configured to:
designate a plurality of points on the first ultrasound slice image; and
calculate a new point on the first ultrasound slice image based on coordinates of the plurality of points;
provide a marker to the new point; and
superimpose the marker on the first ultrasound slice image.

6. The ultrasound diagnostic apparatus according to claim 1,
wherein the processor is configured to:
perform scanning in the three-dimensional space by performing surface scan on a scanning surface with respect to a plurality of scanning surfaces; and
set one of the plurality of scanning surfaces to be a second cut surface.

7. The ultrasound diagnostic apparatus according to claim 1, further comprising:
a treatment instrument having a needle shape configured to project at a predetermined angle near the ultrasound vibration elements,
wherein the processor is configured to set the cut surface so that the cut surface includes a center axis of the treatment instrument and the cut surface rotates around the center axis.

8. The ultrasound diagnostic apparatus according to claim 1, further comprising:
a treatment instrument having a needle shape configured to project at a predetermined angle near the ultrasound vibration elements,
wherein the processor is configured to set the cut surface so as to include a center axis of the treatment instrument and to be orthogonal to the center axis.

9. A method comprising:
setting scan conditions comprising an amount of delay related to drive timing of two-dimensionally arranged ultrasound vibration elements of an ultrasound transducer;
driving the ultrasound vibration elements based on the scan conditions to generate an ultrasound beam;
scanning a plane by transmitting and receiving the ultrasound beam multiple times while changing the direction of the ultrasound beam; and
acquiring an ultrasound slice image of the plane along a sound axis of the ultrasound beam, based on ultrasound data acquired by the scanning,
wherein the method comprises:
acquiring a plurality of ultrasound slice images by scanning a plane multiple times in a three-dimensional space while changing the direction of the plane;
forming three-dimensional volume data based on the plurality of the ultrasound slice images;
receiving an instruction for setting a position of a cut surface, and setting, based on the received set position of the cut surface, the cut surface at the position comprising a position of a surface intersecting with the sound axis;

generating a first ultrasound slice image of the cut surface from the three-dimensional volume data; and determining a focal length of the ultrasound beam or a focal depth of the ultrasound beam according to a distance from the ultrasound transducer to an arbitrary point on the cut surface, and wherein the method comprises:

changing the scan conditions comprising the amount of delay based on the determined focal length or focal depth;

driving the ultrasound transducer based on the changed scan conditions, to generate the ultrasound beam such that the arbitrary point enters a focal area;

rescanning the cut surface by successively transmitting and receiving the ultrasound beam such that the arbitrary point enters the focal area, while moving a position of the arbitrary point from a position of a certain one point of a plurality of points evenly arranged on the cut surface to a position of another one point of the plurality of points; and generating a second ultrasound slice image of the cut surface based on ultrasound data acquired by the rescanning, the second ultrasound slice image being different from the first ultrasound slice image.

\* \* \* \* \*